(12) United States Patent
Imura

(10) Patent No.: US 7,286,215 B2
(45) Date of Patent: Oct. 23, 2007

(54) LIGHT MEASURING APPARATUS AND A METHOD FOR CORRECTING NON-LINEARITY OF A LIGHT MEASURING APPARATUS

(76) Inventor: Kenji Imura, 3-91, Daisennishi-machi, Sakai-shi, Osaka 590-8551 (JP)

( * ) Notice: Subject to any disclaimer, the term of this patent is extended or adjusted under 35 U.S.C. 154(b) by 388 days.

(21) Appl. No.: 10/841,189

(22) Filed: May 6, 2004

(65) Prior Publication Data
US 2005/0128475 A1   Jun. 16, 2005

(30) Foreign Application Priority Data
Nov. 21, 2003   (JP) ............................. 2003-392456

(51) Int. Cl.
*G01J 1/10* (2006.01)
(52) U.S. Cl. ..................... 356/229; 356/213; 356/300
(58) Field of Classification Search ................ 356/300, 356/229, 323, 213, 217, 226, 307, 309; 250/205, 250/214 A, 214 R
See application file for complete search history.

(56) References Cited

U.S. PATENT DOCUMENTS

| 4,537,510 A | 8/1985 | Takahasi |
| 5,229,838 A | 7/1993 | Ganz et al. |
| 6,567,160 B1 * | 5/2003 | Ishikawa et al. ............ 356/229 |

FOREIGN PATENT DOCUMENTS

| JP | 58-103625 | 6/1983 |
| JP | 03-46351 | 9/1991 |
| JP | 05-142041 | 6/1993 |
| JP | 05-297142 | 11/1993 |
| JP | 06-331431 | 12/1994 |
| JP | 05-81849 | 11/1996 |
| JP | 2002-174551 | 6/2002 |

OTHER PUBLICATIONS

"Notice of Reasons for Rejection," (Office Action) for Japanese Patent Application No. 2003-392456, issued Oct. 4, 2005, 5 pages.
"Notice of Reasons for Rejection," Japanese Patent Office Action for Japanese Patent Application No. JP 2003-392456, mailed Jul. 18, 2006, 4 pages.

\* cited by examiner

*Primary Examiner*—L. G. Lauchman

(57) ABSTRACT

A correction LED is provided to illuminate a light receiving sensor array, and a calculation controlling circuit calculates correction values at the respective illuminance levels based on sensor output levels expected at the respective illuminance levels and actual sensor output levels while successively turning the correction LED on at a plurality of illuminance levels whose illuminance ratios are at least known, and corrects a sensor output level by the corresponding correction value to obtain a measurement output at the time of an actual measurement. The discontinuity of an input/output characteristic resulting from the switching of gains of an amplifier for amplifying a photocurrent and the non-linearity caused by the saturation of the photoelectrically converting characteristic of the optical sensor and the exponential characteristics of the optical sensor and the amplifier can be corrected without employing a large-scale construction such as a bench. The non-linearity can be highly precisely and efficiently corrected in a measuring apparatus realized as a spectral luminometer or a spectral colorimeter without requiring a special facility.

8 Claims, 12 Drawing Sheets

| T=200ms | | | | |
|---|---|---|---|---|
| SENSOR OUTPUT | S1 | S2 | · · · | Sn |
| CORRECTION COEFFICIENT | C1 | C2 | · · · | Cn |

LIGHT MEASURING APPARATUS AND A METHOD FOR CORRECTING NON-LINEARITY OF A LIGHT MEASURING APPARATUS

This application is based on Japanese patent application No. 2003-392456 filed on Nov. 21, 2003, the contents of which are hereby incorporated by references.

BACKGROUND OF THE INVENTION

The present invention relates to a light measuring apparatus adapted to measure the intensity of light being measured and suitably usable as a spectral luminometer or a spectral calorimeter and a method for correcting the non-linearity of such a light measuring apparatus.

A polychrometer for simultaneously measuring spectral intensities of all the wavelengths in a measurement wavelength range is widely used as the one of a spectral luminometer (spectral intensity measuring apparatus) for measuring a spectral intensity distribution of light being measured or as the one of a spectral calorimeter (spectral reflection characteristic measuring apparatus) for measuring a spectral reflection characteristic of a sample due to its high measurement efficiency, its capability of measuring an instant light and other factors. FIG. 16 is a sectional view showing a schematic construction of a polychrometer 1 generally in use. The polychrometer 1 includes an incidence opening 3 formed in a housing 2, a light receiving sensor array 4, a diffraction grating 5 and a focusing optical system 6 for forming a wavelength-dispersed image of the incidence opening 3 by a beam having passed the incidence opening 3 on the light receiving sensor array 4. An output from the light receiving sensor array 4 is used to obtain the spectral intensity distribution or the spectral reflection characteristic by a calculation controlling circuit 8 after being subjected to a current-to-voltage conversion in a signal processing circuit 7.

FIG. 17 is a block diagram showing an exemplary construction of the signal processing circuit 7. The light receiving sensor array 4 is an array of (n) photodiodes and output currents of the respective photodiodes d1 to dn are converted into voltage values and amplified in accordance with a high gain by individually provided amplifiers a11 to a1n. In the following description, suffixes 1 to n are attached in the case of showing the constructions of n channels corresponding to the photodiode array comprised of (n) pixels, whereas these suffixes are not attached in the case that it is not necessary to particularly specify the channels. Outputs of the respective amplifiers a11 to a1$n$ are inputted to a multiplexer 9, which successively selects and outputs the outputs from the respective amplifiers a11 to a1n in response to a switch signal from the calculation controlling circuit 8. The output of the multiplexer 9 is amplified by a variable gain amplifier a2 after passing an input resistor r3, then converted into a digital value in an analog-to-digital converter 10, and consequently inputted to the calculation controlling circuit 8.

In the polychrometer 1 constructed as above, the gain of the signal processing circuit 7 is switched in accordance with an amount of an incident light in order to ensure a wide measurement range required for a spectral luminometer. To this end, two kinds of feedback resistors r1, r2 are provided for each amplifier a1 and three kinds of feedback resistors r4, r5, r6 are provided for the variable gain amplifier a2. These feedback resistors r1, r2, r4, r5, r6 are controllably switched by changeover switches s1, s2, s4, s5, s6 provided in series in response to a control signal from the calculation controlling circuit 8 to switch the gains. A ratio of resistance values of the feedback resistor r1 and r2 is, for example, 1:8. A ratio of resistance values of the feedback resistors r4, r5, r6 is, for example, 1:2:4.

Accordingly, in this signal processing circuit 7, the respective gains can be switched to become substantially twofold; a ratio of a minimum gain G=1 to a maximum gain G=6 is about 1:32; and each gain is applied to incident light intensities between a full-scale incident light intensity If(G) and a full-scale incident light intensity If (G-1) of the gain one below the former one as shown in TABLE-1 below.

TABLE 1

| Gain Number | 1 | 2 | 3 | 4 | 5 | 6 |
|---|---|---|---|---|---|---|
| Resistance to be Selected | R1 * R4 | R1 * R5 | R1 * R6 | R2 * R4 | R2 * R5 | R2 * R6 |
| Gain | 1 | 2 | 4 | 8 | 16 | 32 |
| Incident light Intensity Range | I ≤ If1 | If1 < I ≤ If2 | If2 < I ≤ If3 | If3 < I ≤ If4 | If4 < I ≤ If5 | If5 < I ≤ If6 |

However, if the resistance value is switched in a stepwise manner as described above, input/output relationships at the respective gains become discontinuous and cannot be linear as shown in FIG. 18 because of the deviation of the resistance values from nominal values. Accordingly, outputs by the respective gains need to be corrected by their gain ratios in order to obtain linear input/output relationships over the entire dynamic range (measurement range). For instance, using a ratio of outputs obtained by measuring the same incident light intensity in accordance with two adjacent gains as a correction value, a corrected output can be obtained by multiplying an actual measurement value by this correction value. In order to improve a measurement precision, it is desirable to measure the incident light intensity using higher gains approximate to, but not exceeding the full scale.

On the other hand, silicon photosensors in which the amplifiers a11 to a1n for current-to-voltage conversion are individually provided for the respective photodiodes d1 to dn as described above have a sufficiently linear input/output characteristic in a current short-circuit mode. However, electric charge storing sensor arrays of a self scanning type such as CCD have come to be frequently used as the light receiving sensor array 4 of the polychrometer 1 in recent years since they need not have such a processing circuit for each wavelength and is easy to miniaturize. Such CCD have an S-shaped input/output relationship due to its characteristics such as the saturation of a photoelectrically converting characteristic as shown in FIG. 19 and, hence, has a problem of not having linearity normally required for measuring apparatuses.

Accordingly, in the case of using such a light receiving sensor array 4 in a measuring apparatus such as a spectral luminometer, the aforementioned discontinuity and non-linearity such as an S-shaped characteristic have to be corrected by a certain method. Regardless of whether such a correction is made using a look-up table or functional approximation, output data at a plurality of different incident light intensities are necessary as base data. Particularly in order to obtain precise linearity required for a measurement range of a luminometer extending over $10^6$, measurement data at a multitude of incident light intensities within the measurement range are necessary since outputs of the luminometer are largely deviated from a straight line in a low illuminance area and a high illuminance area. A correction value is calculated from the obtained data and a sensor output is obtained by correcting a measurement value by the correction value at the time of an actual measurement. The non-linearity may differ from element to element and from pixel to pixel even in one element. Thus, for a highly precision measurement, correction needs to be made for each element or for each pixel.

Upon obtaining the data for correction, it has been a conventional practice to adjust the intensity of light beams from a white light source to be incident on a measuring apparatus to be corrected. A white light is used because beams of different wavelengths are incident on the respective pixels of the light receiving sensor array 4. Specifically, the incident light intensity is adjusted as follows:

1. Change a distance from the light source.
2. Change a drive voltage for the light source.
3. Insert an ND filter as disclosed in Japanese Unexamined Patent Publication NO. 2002-174551.

The technique 1 of changing the distance from the light source is such that, taking advantage of the fact that a light amount is in inverse proportion to the square of the distance, the measuring apparatus to be corrected is placed on a bench, the distance is changed, and levels of output signals at the respective distances are measured to obtain a correction value.

The technique 2 of changing the drive voltage for the light source is such that a drive voltage or current to be applied to a light emitting element facing the measuring apparatus to be corrected is changed, and levels of output signals at the respective current values or voltage values to obtain a correction value.

Further, the technique 3 of inserting the ND filter is such that the ND filter for light attenuation is inserted between the measuring apparatus to be corrected and the light emitting element, and levels of output signals at light attenuation rates are measured using filters having different light attenuation rates, thereby obtaining a correction value.

Accordingly, any of the known techniques has problems of necessitating a large facility and requiring considerable labor and time for adjustment. Thus, although correction needs to be made for each element as described above, it is a present situation that some of the elements are sampled and a representative correction value obtained from the sampled elements is set.

Further, in such a construction provided with a multitude of pixel sensors such as a spectral luminometer or a spectral colorimeter, it is desirable to switch the gain at an earliest stage of the signal processing in view of a S/N ratio at a low incident light intensity. In the construction in which the amplifiers a1 are provided for the respective pixel sensors as shown in FIG. 17, gains differ for the respective pixel sensors of the light receiving sensor array 4. Thus, the above correction needs to be made for each channel, i.e. for each wavelength.

Since the intensity of the light source and the sensitivity of the light receiving sensor array 4 also depend on wavelength, measurement conditions need to be set for the respective pixel sensors for receiving a measurement light separated according to wavelength, which leads to huge labor and time for correction. In other words, if a white light for correction is caused to be incident on a measuring apparatus to be corrected, divided light beams are incident on the respective pixels, whereby the illuminances and the signal outputs of the respective pixels largely differ by being influenced by spectral characteristics of optical elements such as diffraction gratings and CCD. Thus, measurements need to be made at a larger number of incident light intensities in order to illuminate the respective pixels with illuminances suitable for correction.

Further, in order to cover a wide dynamic range and ensure a proper S/N ratio in the low luminance area, the measurement is conducted by extending an electric charge storing time in the CCD. In the case of elements whose non-linearity differs depending on the electric charge storing time, a measurement data at a necessary illuminance level is required for the respective integration times. This disadvantageously leads to even more labor and time required to measure a non-linearity correction.

SUMMARY OF THE INVENTION

An object of the present invention is to provide a light measuring apparatus and non-linearity correcting method which can highly precisely and efficiently correct the non-linearity of the light measuring apparatus without necessitating a special facility.

According to an aspect of the present invention, one or more correction light emitters is driven at a plurality of illuminance levels whose illuminance ratios are at least known at the time of a correction to illuminate an optical sensor at the plurality of illuminance levels. Correction values at the respective illuminance levels are calculated based on sensor output levels expected at the respective illuminance levels and actual sensor output levels. At the time of an actual measurement, the sensor output level is corrected by the corresponding correction value to obtain a measurement output.

These and other objects, features and advantages of the present invention will become more apparent upon a reading of the following detailed description and accompanying drawings.

DETAILED DESCRIPTION OF THE PREFERRED EMBODIMENTS OF THE INVENTION

First Embodiment

Figure 1:
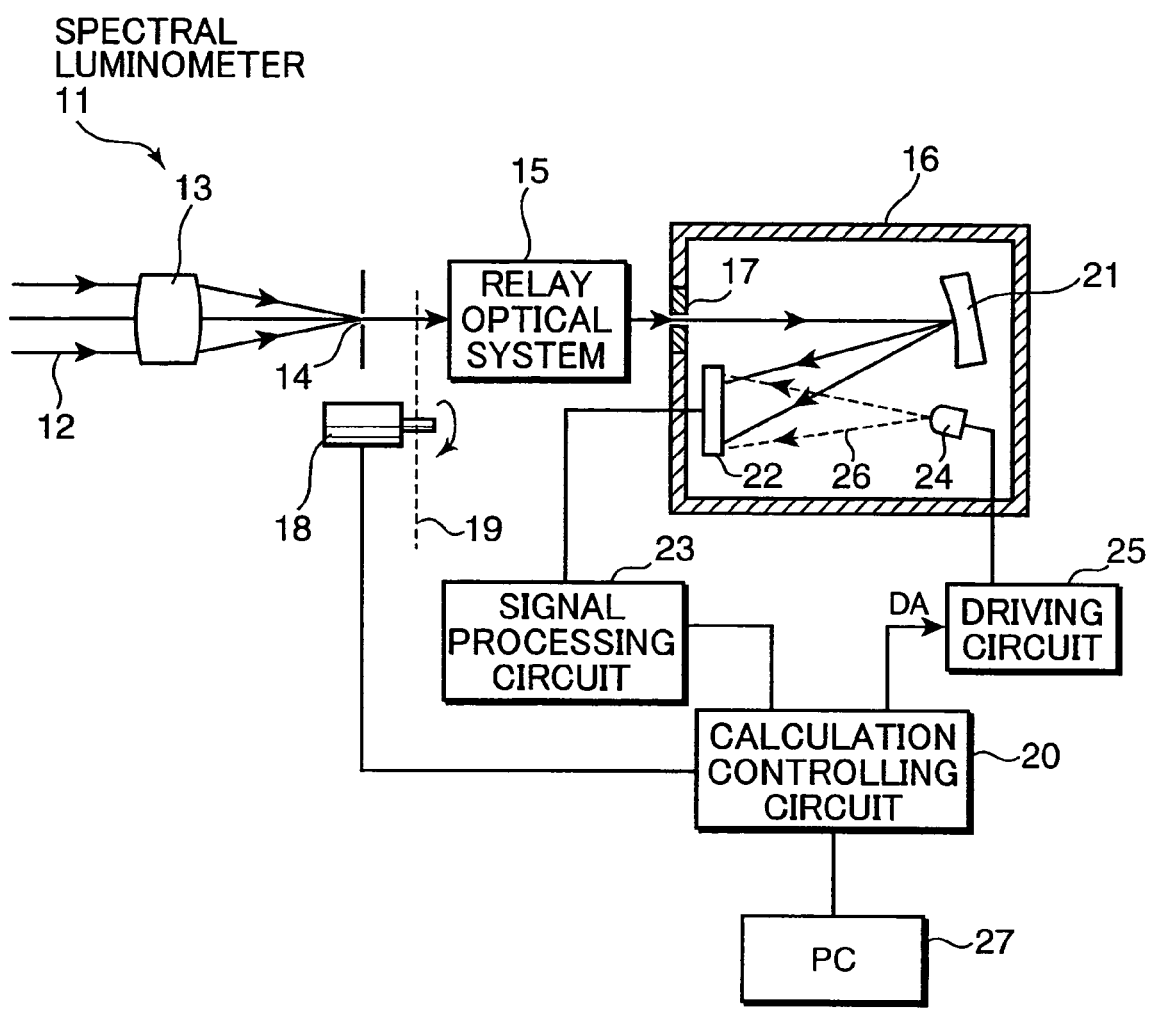
FIG. 1 is a block diagram showing a construction of a spectral luminometer according to a first embodiment of the invention.
Figure 18:
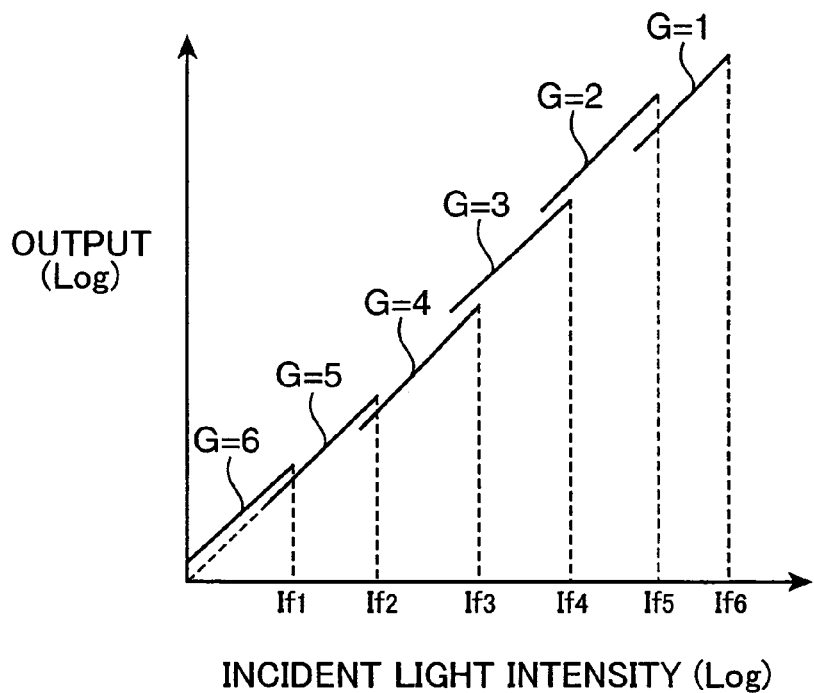
FIG. 18 is a graph showing the discontinuity of an input/output characteristic resulting from the switching of a gain of an amplifier.
Figure 19:
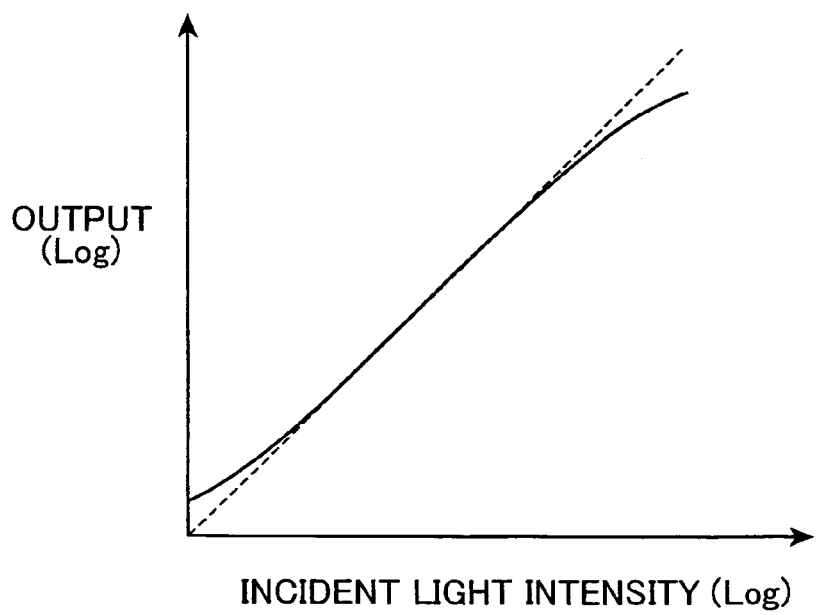
FIG. 19 is a graph showing an exemplary input/output characteristic of a CCD.

FIG. 1 is a block diagram showing a construction of a spectral luminometer 11 according to a first embodiment of the present invention. This spectral luminometer 11 has a function of correcting the discontinuity of an input/output characteristic resulting from the switching of a gain as shown in FIG. 18. Light being measured or measurement light 12 is converged toward a measurement area restricting opening 14 by a light receiving optical system 13 and is caused to form an image of the measurement area restricting opening 14 and converged toward an incidence opening 17 of a polychrometer 16 by a relay optical system 15. A shutter 19 driven by a driving device 18 is provided behind the measurement area restricting opening 14. The driving device 18 is controlled by a calculation controlling circuit 20. The shutter 19 is closed while no measurement is conducted and while a correction to be described later is made, whereas it is opened during a measurement to control the incidence of the measurement light 12.

In this way, the measurement light 12 incident on the incidence opening 17 is incident on a concave diffraction grating 21 to be dispersed and reflected in different directions according to wavelength, thereby forming a dispersed image of the incidence opening 17 on a light receiving sensor array 22 in which a plurality of pixel sensors such as silicon photodiodes are arranged at even intervals as described later. In order to eliminate the influence of secondary diffracted lights by the concave diffraction grating 21, secondary light removing filters (short-wavelength area eliminating filters) may be provided before the pixels in a long wavelength area of the light receiving sensor array 22 (not shown). Outputs of the respective pixel sensors of the light receiving sensor array 22 are fed to the calculation controlling circuit 20 after being subjected to processings in a signal processing circuit 23. The calculation controlling circuit 20 processes the output signals of the pixel sensors to calculate and output a spectral intensity of the measurement light 12. A personal computer 27 is connected with the calculation controlling circuit 20 at the time of a correction to be described later.

What should be noted here is that this polychrometer 16 is provided with a correction LED 24. This correction LED 24 is caused to blink and has its spectral luminance level controlled by the calculation controlling circuit 20 via the driving circuit 25, and an output light 26 thereof is a directly reaching light and evenly illuminates all the pixel sensors of the light receiving sensor array 22 without by way of the concave diffraction grating 21. An infrared LED is desirably used as the correction LED 24 in view of a small forward voltage of about 1.2V, the capability of its emitted light to transmit through the secondary light eliminating filter and a high sensor sensitivity.

Figure 2:
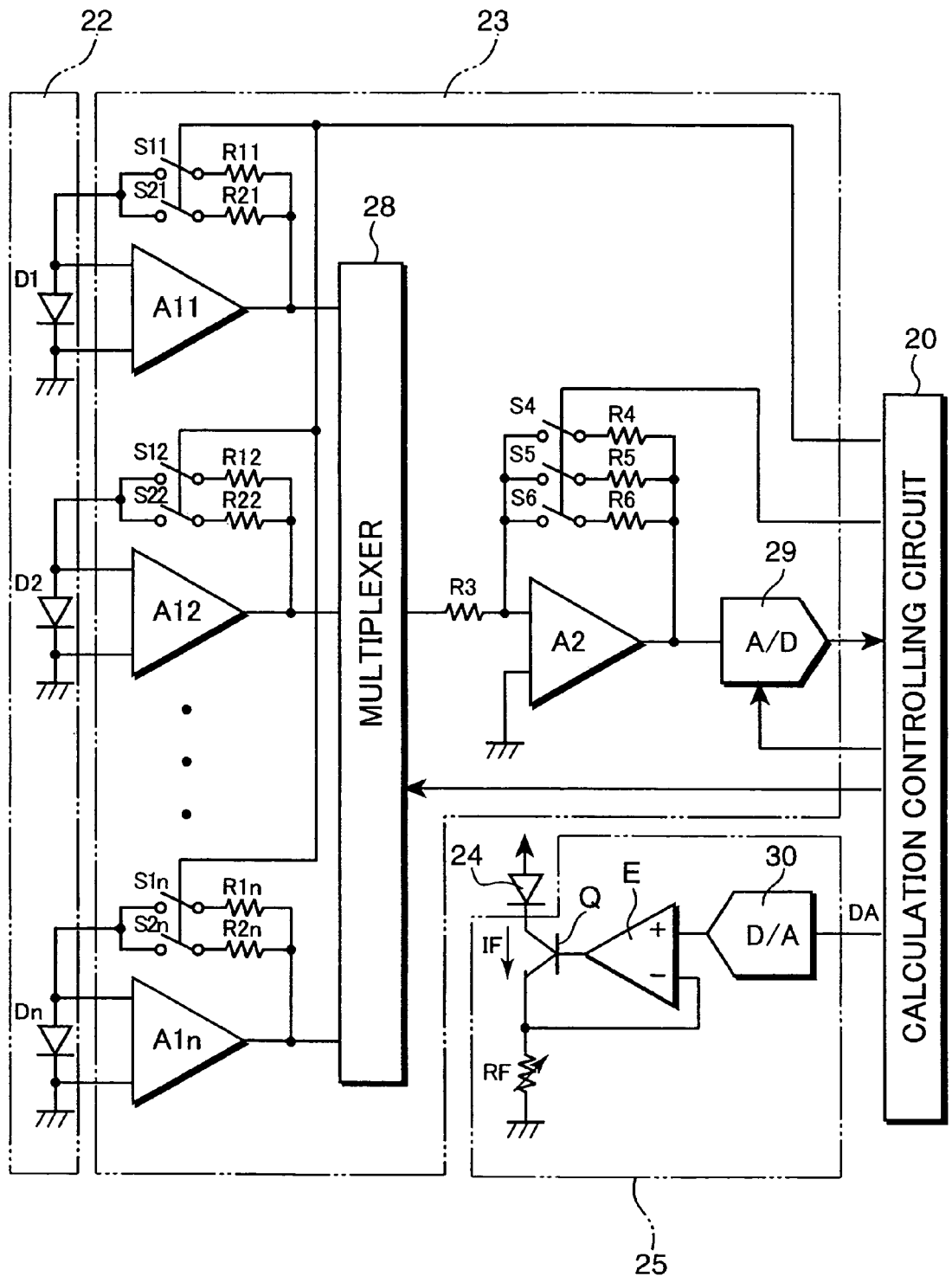
FIG. 2 is a block diagram showing a specific construction of a signal processing circuit and a driving circuit in the spectral luminometer shown in FIG. 1.
Figure 3:
FIG. 3 is a front view showing an arrangement of pixel sensors of a light receiving sensor array in the spectral luminometer shown in FIG. 1.
Figure 17:
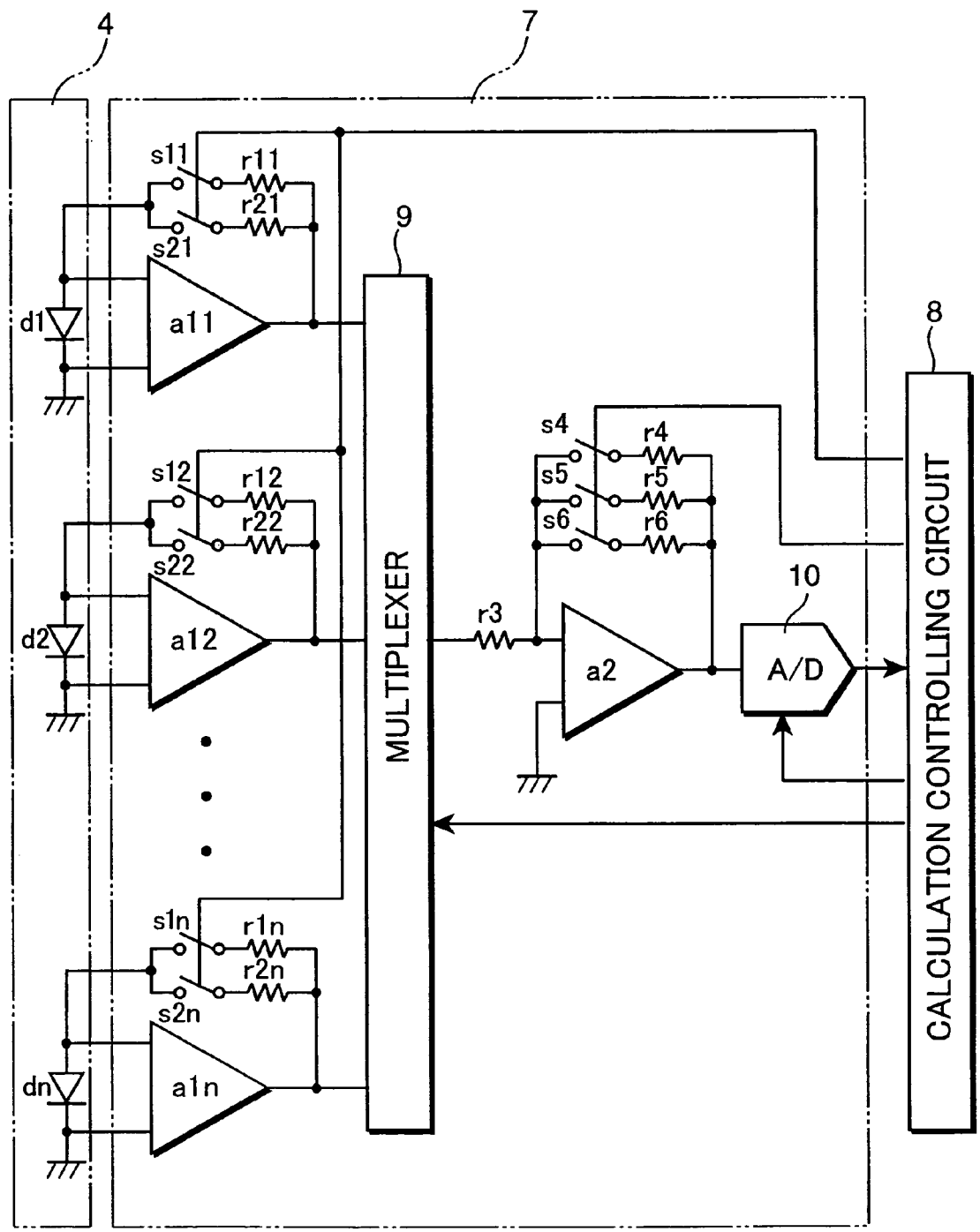
FIG. 17 is a block diagram showing an exemplary construction of a signal processing circuit in the polychrometer shown in FIG. 11.

FIG. 2 is a block diagram showing a specific construction of the signal processing circuit 23 and the driving circuit 25. The signal processing circuit 23 is basically constructed in the same manner as the aforementioned signal processing circuit 7 shown in FIG. 17. Accordingly, the light receiving sensor array 22 is comprised of n silicon photodiodes, and output currents from photodiodes D1 to Dn which are pixel sensors are converted into voltage values by individually provided amplifiers A11 to A1n and amplified with a high gain as also shown in FIG. 3. Outputs of the respective amplifiers A11 to A1n are inputted to a multiplexer 28, which successively selects and outputs the outputs from the respective amplifiers A11 to A1n one by one in response to a switch signal from the calculation controlling circuit 20. Outputs from the multiplexer 28 are converted into digital values in an analog-to-digital (A/D) converter 29 and outputted to the calculation controlling circuit 20 after passing an input resistor R3 and being amplified by a variable gain amplifier A2.

In order to switch a gain of the calculation controlling circuit 20 according to an amount of the incident light upon obtaining a wide measurement range required for the spectral luminometer, two kinds of feedback resistors R1, R2 are provided for each amplifier A1 and three kinds of feedback resistors R4, R5, R6 are provided for the variable gain amplifier A2. These feedback resistors R1, R2; R4, R5, R6 are controllably switched by changeover switches SW1, SW2; SW4, SW5, SW6 provided in series in response to a control signal from the calculation controlling circuit 20 to switch the gains. A ratio of resistance values of the feedback resistor R1 and R2 is, for example, 1:8. A ratio of resistance values of the feedback resistors R4, R5, R6 is, for example, 1:2:4.

Accordingly, in this signal processing circuit 20, the respective gains can be switched to become substantially twofold; a ratio of a minimum gain G=1 to a maximum gain G=6 is about 1:32 (from $2^0$ to $2^6$); and each gain is applied to incident light intensities between a full-scale incident light intensity If(G) and a full-scale incident light intensity If(G-1) of the gain one below the former one as shown in the above TABLE-1. The above points are same as in the aforementioned signal processing circuit 7. An output of the variable gain amplifier A2 is converted into a digital signal of 16 bits, i.e. $2^{16}$ gradations at full scale, by the A/D converter 29 of 16 bits. A dynamic range of $2^{22} \approx 4*10^6$ gradations can be covered by such gain selection and A/D conversion.

The driving circuit 25 includes a digital-to-analog (D/A) converter 30, an error amplifier E, a transistor Q and a current detecting resistor RF. An anode of the correction LED 24 is connected with a power supply of high level, whereas a cathode thereof is grounded via the transistor Q and the current detecting resistor RF. An LED control data DA outputted from the calculation controlling circuit 20 is converted into a voltage signal VDA by the D/A converter 30 and inputted to a (+) input terminal of the error amplifier E. A drive current IF of the correction LED 24 via the transistor Q is inputted to a (−) input terminal of the error amplifier E after being converted into a voltage value by the current detecting resistor RF, and a base current of the transistor Q is controlled by an output of this error amplifier E. In this way, the drive current IF of the LED 24, i.e. emission luminance is controlled to a level in conformity with the LED control data DA outputted from the calculation controlling circuit 20.

Since optical characteristics of optical components of the spectral luminometer 11 constructed as above, spectral sensitivities of the sensors thereof and circuit characteristics differ from luminometer to luminometer, the spectral luminometer 11 is individually calibrated using a standard light source having a reference spectral intensity. Since this calibration is normally a one-point calibration, non-linearity needs to be corrected beforehand. On the other hand, gain characteristics of the amplifiers A1, A2 are not linear as shown in FIG. 18 by the switching of the feedback resistors R1, R2; R4, R5, R6 due to deviations of actual ratios of the resistance values of the feedback resistors R1, R2; R4, R5, R6 from nominal values. Thus, the ratios of the respective gains are calculated before the above sensitivity correction, and the non-linearity is corrected as follows so that an input/output relationship of each pixel sensor is linear.

Upon a correction, the spectral luminometer 11 is connected with the personal computer 27 and is controlled via the calculation controlling circuit 20 by a correction program on the personal computer 27. This correction program is saved by, with the shutter 19 closed, sending a plurality of different LED control data DA to the driving circuit 25, causing the correction LED 24 to emit at a plurality of different intensities and measuring the outputs of the respective pixel sensors of the light receiving sensor array 22 illuminated by the output light of the LED 24 in accordance with a plurality of gains of the signal processing circuit 23.

Specifically, when the LED control data DA is of full scale ($2^{12}$), hence, the correction LED 24 emits light at its maximum luminance, an output of the light receiving sensor array 22 in response to the output light of the LED 24 is processed in accordance with a minimum gain in the signal processing circuit 23 and the resistance value of the current detecting resistor RF of the driving circuit 25 is adjusted so that the A/D conversion results of the outputs of all the pixel sensors take approximate values within the full scale.

Subsequently, the LED control data DA is increased at an interval of 1 ($2^0$) from 1 ($2^0$) to 8 ($2^3$), and then increased at an interval of 2 ($2^1$) from $2^3$ to $2^4$. Hereafter, the LED control data DA is increased at an interval of $2^{n-2}$ from $2^n$ to $2^{n+1}$ (n=integer from 2 to 11). The outputs of the respective pixel sensors illuminated by the output light of the LED 24 using the LED control data DA in these 40 steps are measured in accordance with the respective gains G and saved as data Di(G, DA). Data Di(G, DAmax) closest, but not exceeding the full scale at the respective gains G are searched from the saved data Di (G, DA) with respect to the respective pixels i (e.g. i=1 to 40), and data Di(G-1, DAmax) closest, but not exceeding the full scale at gains one below the former ones are further searched. Correction coefficients Ri(G) are successively calculated from the data of the adjacent gains as follows and saved.

$$Ri(G)=Di(G, DAmax)/Di(G\text{-}1, DAmax)$$

A detailed procedure of an inter-gain error correction is described below.

1. Close the shutter 19.
2. Measure and save offset signals OS(G) of the respective gains of each pixels i.
3. Set n=3.
4. Output the LED control data DA=1 to the D/A converter 30 and turn the correction LED 24 on.
5. Measure the signal Di(G) of the respective gains G of each pixel i and save it as a data Di(G, DA) in correspondence with the LED control data DA.
6. Calculate and save Di(G,DA)'=Di(G, DA)−OS(G).
7. Output DA=DA+$2^{n-3}$ to the D/A converter 30, turn the correction LED 24 on and return to 5. if DA<$2^n$.
8. Return to 5. after setting n=n+1 if n<12.
9. Search the data Di'(G, DAmax) most approximate to, but not exceeding the full scale for the respective gains G of each pixel i from the saved data Di(G, DA)'.
10. Search a data Di'(G-1, DAmax) in accordance with the gain G-1 one below using the same LED control data DA.
11. Calculate and save a gain ratio Ri'(G) of each pixel i:Ri'(G)=Di'(G, DAmax)/Di'(G-1, DAmax).
12. Calculate a data on a gain ratio of the respective gains, 1:Ri'(2):Ri'(3):Ri'(4):Ri'(5):Ri'(6) from the saved adjacent gain ratios Ri'(G)(G=2 to 6), and save it in the calculation controlling circuit 20.

Figure 4:
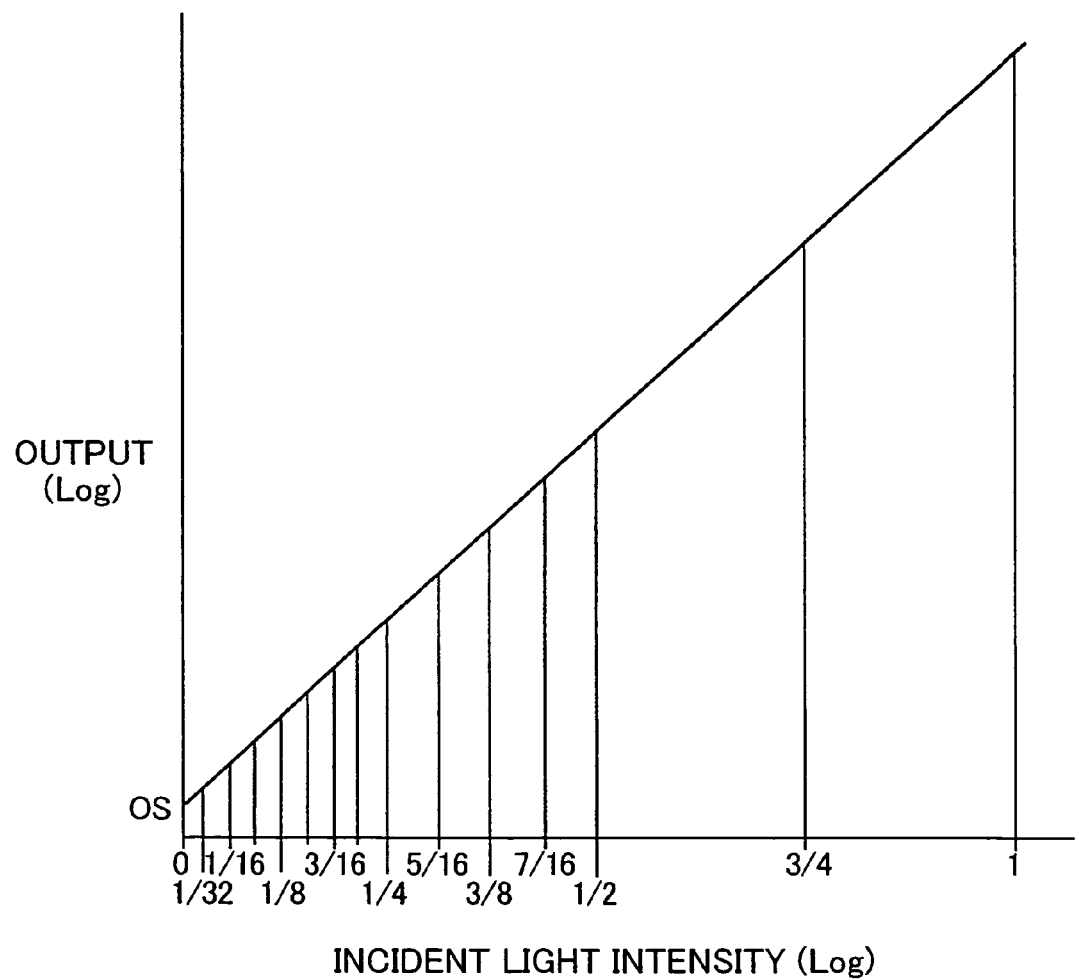
FIG. 4 is a graph showing a data having discontinuity corrected, the discontinuity resulting from the switching of a gain of an amplifier corrected.

At the time of a measurement, the calculation controlling circuit 20 reads the data on the gain ratios Ri'(G) corresponding to the gains G used in the measurement and corrects the output data Di of the respective pixel sensors by Di'=Di/Ri'(G). FIG. 4 shows a data having linearity corrected as described above with n=5, i.e. in 32 gradations.

Next, the operation of the calculation controlling circuit 20 at the time of an actual spectral luminance is described.

1. Measure and save preliminary measurement offset data OSio of the pixels i in according with a minimum gain G0 with the shutter 19 closed.
2. Open the shutter 19.
3. Measure a measurement light in accordance with the minimum gain G0 and save preliminary data Dio of the pixels i.
4. Calculate offset-corrected data Dio'=Dio−OSio.
5. Determine an optimal gain Gi of each pixel from the offset-corrected data Dio'.
6. Measure the measurement light in accordance with the determined gain Gi and save the measurement data Di of each pixel i.
7. Close the shutter 19.
8. Measure the offset data OSi in accordance with the determined gain Gi.
9. Calculate data Di'=(Di−OSi)/Ri'(G) corrected with the gain ratios Ri'(G) corresponding to the offset data OSi and the gains Gi.

Since the gain ratios Ri belong to the resistance values of the feedback resistors R1, R2; R4, R5, R6 of the current-to-voltage converting amplifiers A1 and the variable gain amplifier A2, these gain ratios are subject to a change with time and a thermal change to a very small degree if resistors of suitable grades are used and the correction data obtained at a factory are valid as long as the feedbacks R1, R2; R4, R5, R6 are not replaced. The correction data need to be obtained again in the case of replacing the feedback resistors R1, R2; R4, R5, R6 for repair or the like. However, according to the inventive technology, the aforementioned procedure can be automatically executed within a short time by connecting the spectral luminometer 11 with the personal computer 27 capable of executing a correction program even outside the factory, e.g. at a service point without necessitating any special facility and technology as in the prior art.

In this way, the input/output characteristics are connected into one straight line by using a plurality of gains, whereby the discontinuity of the input/output characteristics can be highly precisely and efficiently corrected without necessitating any special facility.

Further, by providing the shutter 19 for shutting the measurement light 12 off while the correction LED 24 is turned on, the non-linearity can be precisely corrected only based on an illumination light for correction from the correction LED 24 without being influenced by an incident light from the outside. Furthermore, since the illumination light from the correction LED 24 directly reaches the light receiving sensor array 22, all the pixel sensors are uniformly illuminated without reducing the illumination light level only at some particular pixel sensors and, therefore, a precise correction can be conducted within a short time.

The personal computer 27 is connected only at the time of a correction at the service point, factory or the like. Likewise, the correction LED 24 and the driving circuit 25 may be mounted only at the time of a correction.

Second Embodiment

Figure 5:
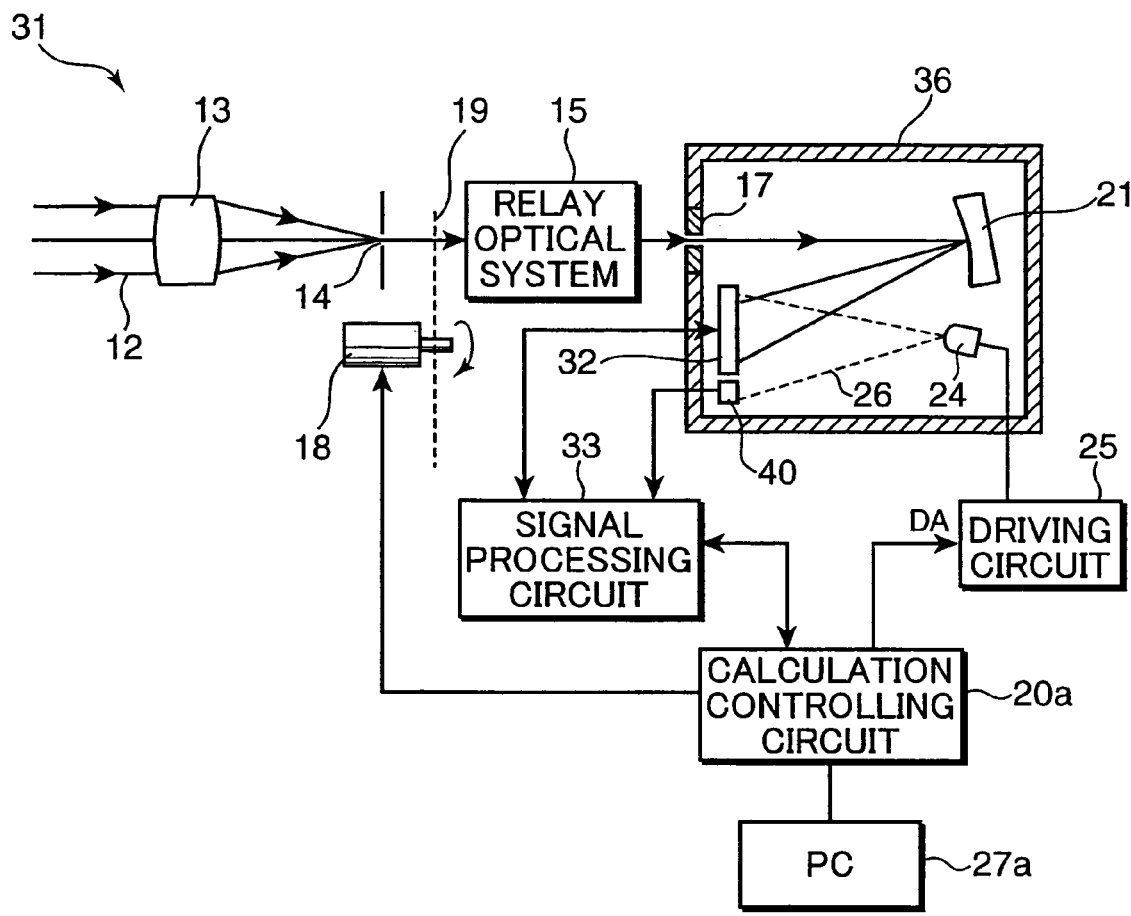
FIG. 5 is a block diagram showing a construction of a spectral luminometer according to a second embodiment of the invention.

FIG. 5 is a block diagram showing a construction of a spectral luminometer 31 according to a second embodiment of the invention. This spectral luminometer 31 is similar to the aforementioned spectral luminometer shown in FIG. 1, and no description is given on corresponding parts and elements thereof by identifying them by the same reference numerals. What should be noted is that the light receiving sensor array 22 is comprised of silicon photodiodes, the amplifiers Al for the current-to-voltage conversion are provided for the respective photodiodes D1 to Dn as shown in FIG. 2, and the gains (sensitivities) are switched by switching the feedback resistors R1, R2; R4, R5, R6 of the amplifiers A1, A2 in the aforementioned spectral luminometer 11, whereas a light receiving sensor array 32 is a CCD and the gains (sensitivities) are also switched according to integration times of electric charges stored into the CCD in the spectral luminometer 31.

Figure 6:
FIG. 6 is a front view showing an arrangement of pixel sensors of a light receiving sensor array in the spectral luminometer shown in FIG. 5.

Accordingly, this spectral luminometer 31 has a function of correcting S-shaped characteristics of the CCD for each integration time. The light receiving sensor array 32 is comprised of pixels S1 to Sn arranged at n stages as shown in FIG. 6, and the number n of the pixels is for example, 256 (i=1 to 256).

In this spectral luminometer 31, a monitor sensor 40 comprised of silicon photodiodes and adapted to monitor an illumination light from a correction LED 24 is provided in proximity to the light receiving sensor array 32 in a polychromater 36 in order to correct the non-linearity of the CCD. A signal processing circuit 33 corrects the discontinuity of the outputs of this monitor sensor 40 resulting from the switching of the gains of amplifiers as described later as the aforementioned calculation controlling circuit 20 corresponding to the light receiving sensor array 22 comprised of the silicon photodiodes does.

Figure 7:
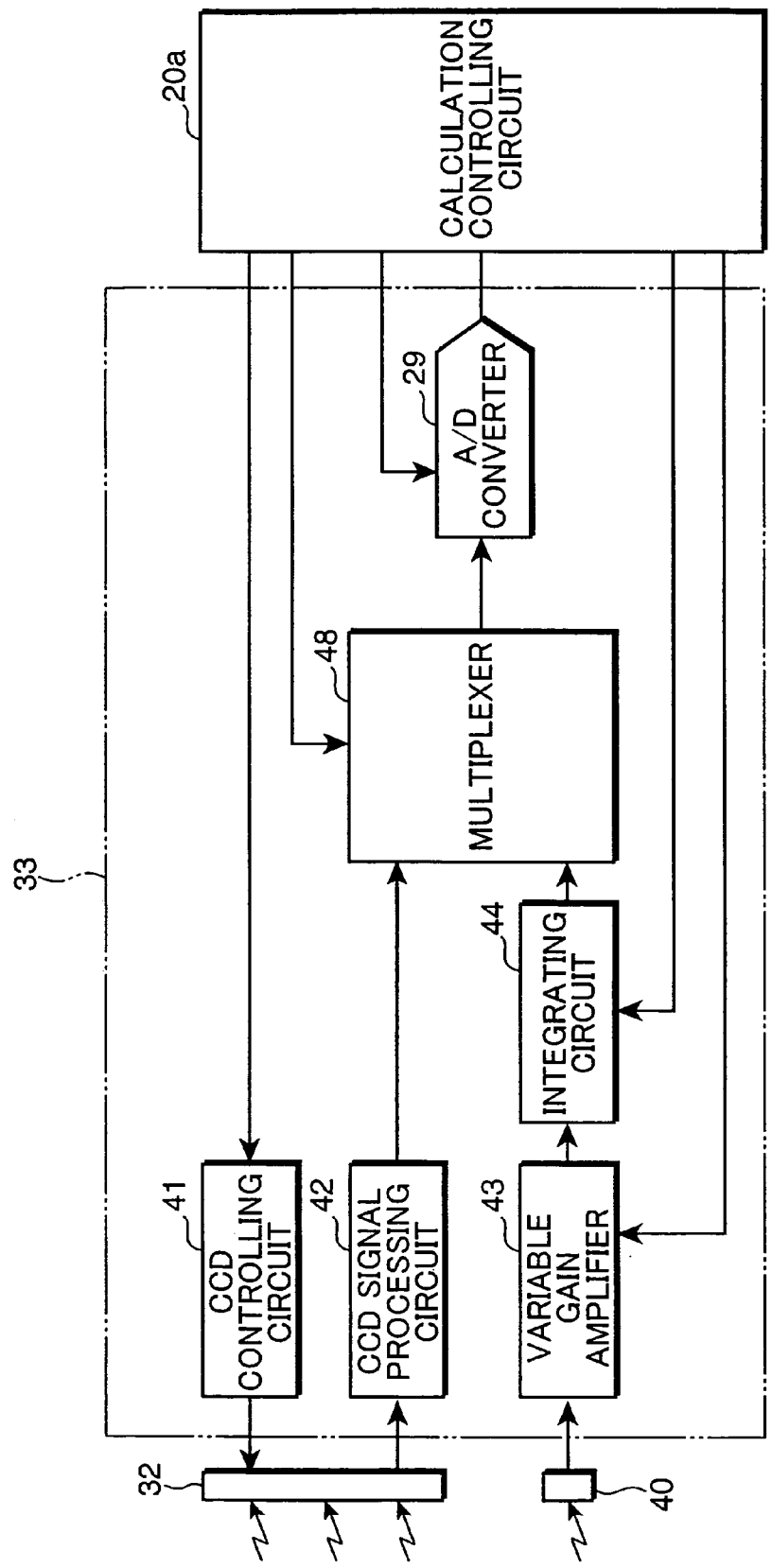
FIG. 7 is a block diagram showing an exemplary construction of a signal processing circuit in the spectral luminometer shown in FIG. 5.

FIG. 7 is a block diagram showing an exemplary construction of the signal processing circuit 33. Clocks necessary for the control are fed from a calculation controlling circuit 20a to the respective pixels of the light receiving sensor array 32 via a CCD controlling circuit 41, and a CCD signal processing circuit 42 successively reads output signals from the respective pixels in accordance with these clocks, applies signal processing and feeds the resulting signals to an A/D converter 29 via a multiplexer 48. In this way, the outputs from the respective pixels of the CCD are successively converted into the digital signals and inputted to the calculation controlling circuit 20a.

On the other hand, an output from the monitor sensor 40 is integrated in an integrating circuit 44 after being current-to-voltage converted and amplified in a variable gain amplifier 43 including a current-to-voltage converting circuit, and then inputted to the calculation controlling circuit 20a via the multiplexer 48 and the A/D converter 29. Since the CCD integrates a photocurrent of a specified period as described above, the integrating circuit 44 can monitor a light incidence made at the same timing as a light incidence onto the CCD by integrating the output of the variable gain amplifier 43 for the same period as the integration time of the CCD. The gains are switched in order to monitor the illuminance of the measurement range of the spectral luminometer 31. The discontinuity between the gains is corrected by the aforementioned technique employed by the spectral luminometer 11.

In the spectral luminometer 31 constructed as above, the S-shaped characteristics of the CCD are corrected on the basis of the output of the monitor sensor 40 and on the premise that an incident light/output current characteristic of the monitor sensor 40 is sufficiently linear. The incident light/output current characteristics of the silicon photodiodes used in the current short-circuit mode are sufficiently linear, and there is no problem in correcting the above S-shaped characteristic on the basis of this for a usual purpose.

A procedure of correcting the S-shaped characteristic is described below. Similar to the spectral luminometer 11, the spectral luminometer 31 is connected with a personal computer 37a and controlled via the calculation controlling circuit 20a by a loaded correction program. Similar to the aforementioned one, the correction program causes a plurality of different LED control data DA to be fed to a driving circuit 25 with a shutter 19 closed, thereby causing the correction LED 24 to emit light at a plurality of different intensities. Illuminances on the pixel surfaces of the pixels S1 to Sn illuminated by emitted lights of a plurality of intensities cover a range illuminance range received within the measurement range of the luminometer.

In the spectral luminometer 31 of this embodiment, noise level becomes $\sqrt{T/N}$ to enable an improvement in S/N ratio if the integration time is multiplied by N for random noises. Thus, the photoelectronic integration time T of the CCD is selectable from T1=50 ms, T2=200 ms, T3=1 s to improve repeatability. Accordingly, the non-linearity is corrected for each integration time T. Thus, the correction program measures and saves outputs $Si(T, DA)$ and outputs $M(T, DA)$ of the monitor sensor 40 during each integration time T for the respective pixels i of the CCD illuminated by the output light of the correction LED 24. Based on the saved data, a correction coefficient $Ci[T, Si(T, DA)]$ is obtained. The correction coefficient $Ci[T, Si(T, DA)]$ is expressed as the following equation:

$$Ci[T, Si(T, DA)] = M(T, DA)/Si(T, DA).$$

In other words, the correction coefficient Ci[T, Si(T, DA)] is such that the data Si (T, DA) of the pixel i corresponding to a certain LED control data DA and obtained during a certain integration time T coincides with the data M (T, DA) of the monitor sensor 40 simultaneously obtained, and is obtained for each pixel i during each integration time T, and is saved in the calculation controlling circuit 20a. The correction program basically operates as above. A deviation from the straight line representing the incident/output characteristic depends on an amount of electric charges stored in the CCD. A procedure is necessary which takes into consideration that the stored electric charges include those produced by the incident light and those produced by something like heat other than the incident light (offset).

Specifically, the procedure of producing the correction data is as follows.

Figures 8, 9:
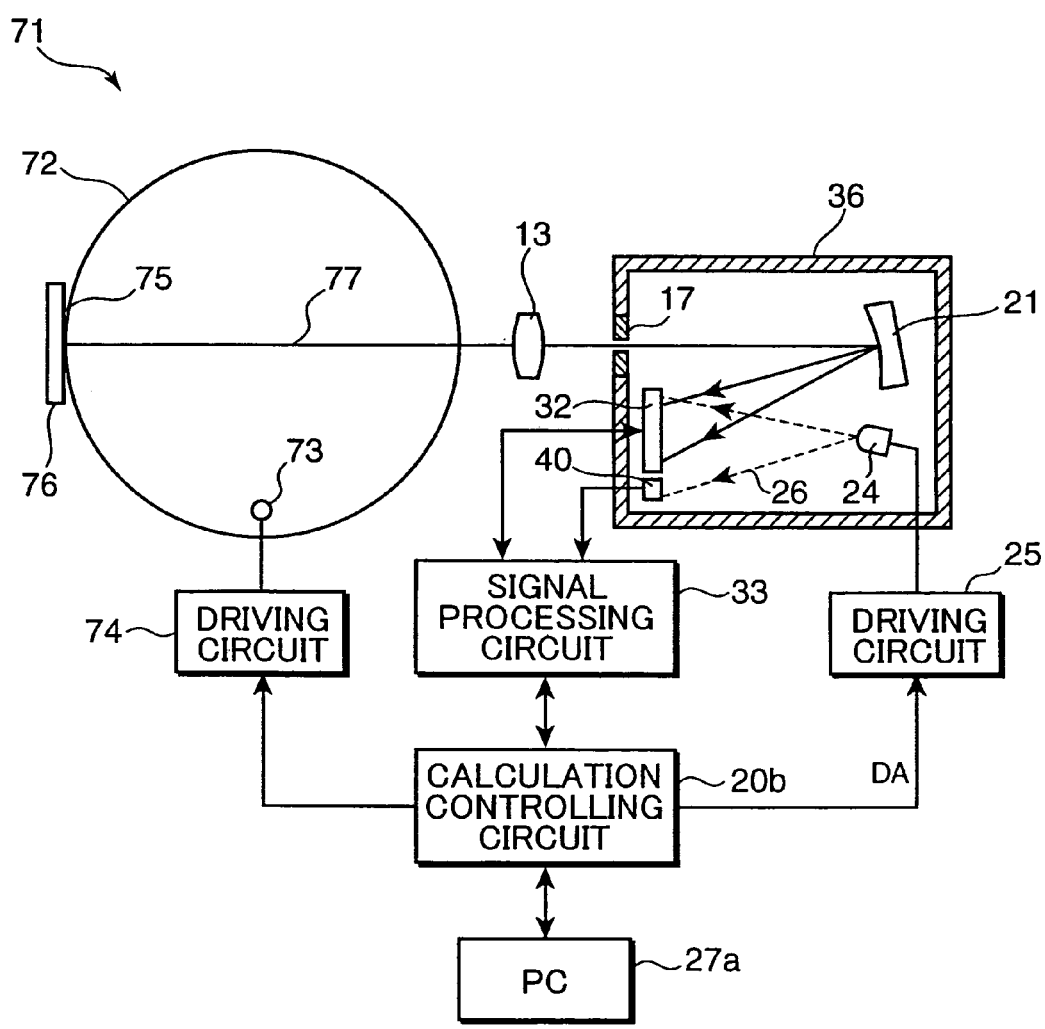
FIG. 8 is a diagram showing an example of a correspondence table of measurement data and correction coefficients.
FIG. 9 a block diagram showing a construction of a spectral luminometer according to a third embodiment of the invention.

1. Close the shutter 19.
2. Measure offset data OSi(T), OSM(T) during the respective selectable integration times T for the respective pixels i and the monitor sensor 40.
3. Set n=3.
4. Output a data DA=1 to the D/A converter 30 to turn the correction LED 24 on.
5. Measure and save the data Si(T, DA), M(T, DA) during the respective integration times T for the respective pixels i and the monitor sensor 40.
6. Calculate and save Si'(T, DA)=Si(T, DA)−OSi(T) and M' (T, DA)=M(T, DA)−OSM(T).
7. Return to 5. after outputting DA=DA+$2^{n-3}$ to the D/A converter 30 to turn the correction LED 24 on if DA<$2^n$.
8. Return to 5. after setting n=n+1 if n<12.
9. Calculate the correction coefficient Ci[T, Si(T, DA)]=M' (T, DA)/Si'(T, DA) for the saved data M'(T, DA)and Si'(T, DA), generate a Si—Ci correspondence table as shown in FIG. 8 for each integration time T, and save the generated tables in the calculation controlling circuit 20a.

Although measurements are conducted for all the selectable integration times with respect to all the LED control data in the above description, if the data S1 to Sn of all the pixels obtained using a certain control data and during a certain integration time are saturated, the data of all the pixels never fail to be saturated for the control data of this level or higher. Therefore, a time required for the generation of the correction data Ci can be shortened by omitting the measurements for this integration time.

At the time of an actual measurement, the calculation controlling circuit 20a saves the output data Si of the respective pixels obtained when measuring the measurement light at the integration time T set by the user. The calculation controlling circuit 20a further calculates the correction coefficient Ci[T, Si] corresponding to the output data Si and the correction coefficients Ci[T, OSi] corresponding to the offset data OSi based on some of the correction coefficient data Ci[T, Si(T, DA)] saved for each integration time T beforehand and corresponding to the set integration time T. Whereupon, data Si' representing the corrected S-shaped characteristic is calculated:

Si'=Ci[T, Si]*Si−Ci[T, OSi]*OSi.

Although the correction coefficients Ci[T, Si], Ci[T, OSi] are calculated by applying a three-dimensional interpolation or a linear interpolation to the saved data, they may be calculated using a suitable other interpolation or a multinominal approximation.

Next, the operation of the calculation controlling circuit 20a at the time of an actual measurement by the spectral luminometer is described.

1. Close the shutter 19.
2. Read the integration time T set by the user.
3. Measure and save the offset data OSi(T) of the respective pixels i for the set integration time T.
4. Open the shutter 19.
5. Measure the measurement light for the set integration time T to measure and save the measurement data Si(=1 to n) of the pixels i.
6. Call the Si-Ci correspondence table corresponding to the integration time T and calculate the correction coefficients Ci(Si) corresponding to Si by the three-dimensional interpolation based on a relationship of four Si closest to Si and their corresponding Ci.
7. Similarly calculate the correction coefficients Ci(OSi) corresponding to the offset data OSi(T).
8. Calculate the offset-corrected and linearity-corrected data Si'=Si*Ci(Si)−OSi*Ci(OSi).

The CCD may display different S-shaped characteristics depending on the pixel or the integration time. The non-linearity can be easily corrected for each integration time and for each pixel by using the inventive technique.

Third Embodiment

FIG. 9 is a block diagram showing a construction of a spectral luminometer 71 according to a third embodiment of the present invention. This spectral luminometer 71 is similar to the aforementioned spectral luminometer 31, and no description is given on the corresponding parts and elements thereof by identifying them by the same reference numerals. This spectral luminometer 71 is further provided with an integrating sphere 72 having a paint of high reflectivity and high dispersing property applied to the inner surface thereof, and a light source 73 provided therein.

When a driving circuit 74 causes the light source 73 to emit light in accordance with an emission control signal from the calculation controlling circuit 20b, this output light is diffused and reflected by the inner surface of the integrating sphere 72 to illuminate a sample 76 placed at a sample opening 75. A component 77 of the light reflected by the sample in an observing direction is received by a light receiving optical system 13 and a polychrometer 36 similar to the aforementioned spectral luminometer 31. The above technique is applicable for the correction of S-shaped characteristics of CCD incorporated into the polychrometer 36. A xenon flash is frequently used as the light source 73 of the spectral luminometer 71. However, the CCD sometimes has non-linearity in response to a pulse light such as light from a xenon flash different from non-linearity in response to a continuous light. A correction LED 24 can have its non-linearity effectively corrected by being turned on by a pulse having the same pulse width as the xenon flash.

Fourth Embodiment

Figure 10:
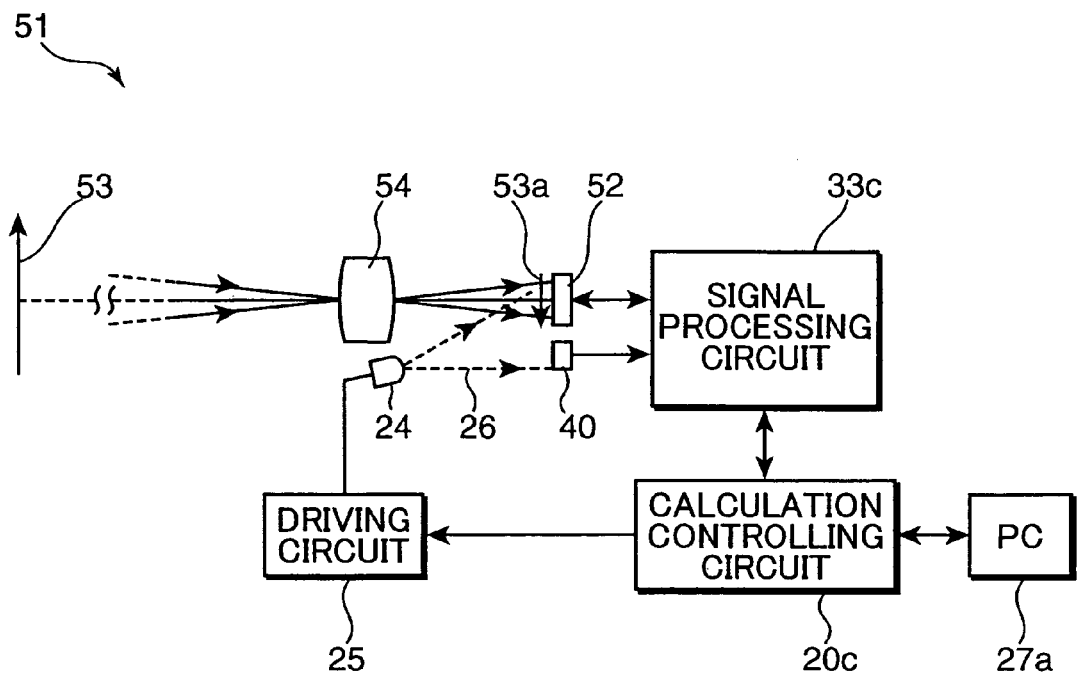
FIG. 10 is a block diagram showing a construction of an image measuring apparatus according to a fourth embodiment of the invention.

FIG. 10 is a block diagram showing a construction of an image measuring apparatus 51 according to a fourth embodiment of the invention. The aforementioned technique of correcting the S-shaped characteristics of the CCD using the monitor sensor 40 is applicable not only for the correction of the linear CCD incorporated into the polychrometer 36 of the spectral luminometer 31 or the spectral luminometer 41, but also for the correction of two-dimensional CCD 52 incorporated into this image measuring apparatus 51. An image 53a of an object 53 is formed on the two-dimensional CCD 52 by an image forming optical system 54, and an obtained photoelectrically converted output is inputted to a calculation controlling circuit 20c via a signal processing circuit 33c to measure a luminance distribution of the object 53. Similar to the spectral luminometers 31, 41, an emission light 26 of the correction LED 24 illuminates all the pixels of the two-dimensional CCD 52 and a monitor sensor 40.

In this way, the non-linearity of many of the pixel sensors of the two-dimensional CCD can be easily corrected by using ratios of outputs of the monitor sensor 40 at the respective illuminance levels to outputs of the respective pixel sensors of the two-dimensional CCD 52.

Fifth Embodiment

Figure 11:
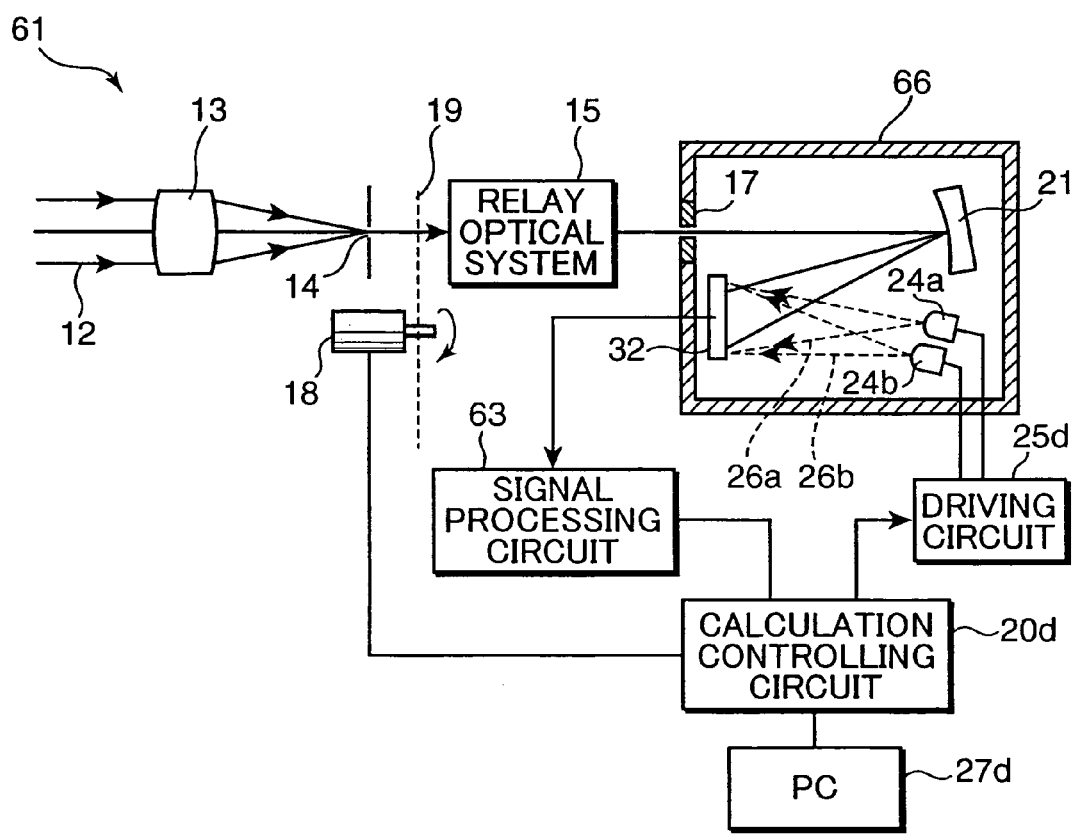
FIG. 11 is a block diagram showing a construction of a spectral luminometer according to a fifth embodiment of the invention.

FIG. 11 is a block diagram showing a construction of a spectral luminometer 61 according to a fifth embodiment of the present invention. This spectral luminometer 61 is similar to the aforementioned spectral luminometer 31 shown in FIG. 5 and no description is given on corresponding parts and elements thereof by identifying them by the same reference numerals. This spectral luminometer 61 also has a function of correcting an S-shaped characteristic of a light receiving sensor array 32 of CCD. What should be noted is that no monitor sensor 40 is provided in a polychrometer 66, two correction LEDs 24a, 24b are provided instead and individually blinked and have their emission luminance levels controlled by a calculation controlling circuit 20d via a driving circuit 25d. Emission lights 26a, 26b from the correction LEDs 24a, 24b are uniformly emitted to the respective pixels S1 to Sn of the light receiving sensor array 32.

Figure 12:
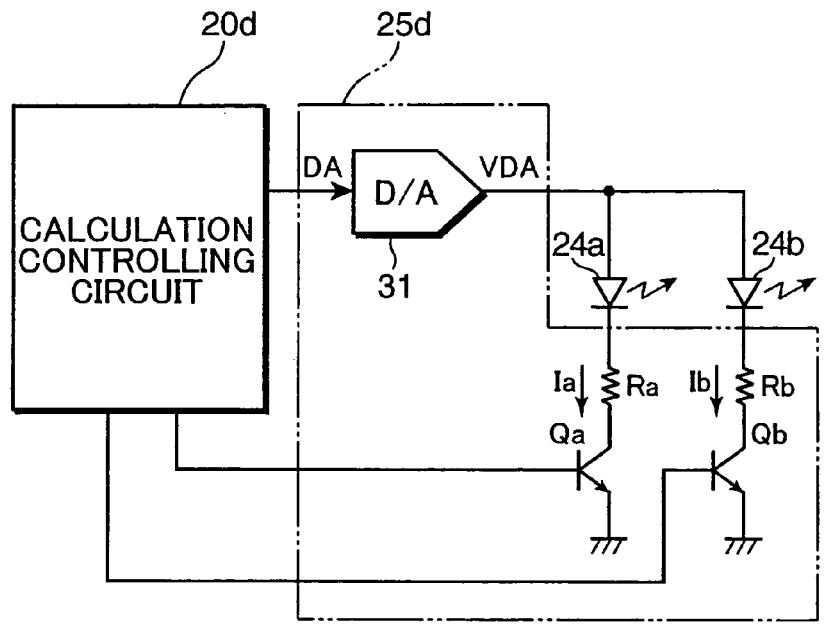
FIG. 12 is an electric circuit diagram showing a specific construction of a driving circuit in the spectral luminometer shown in FIG. 11.

FIG. 12 is an electrical circuit diagram showing a specific construction of the driving circuit 25d. A LED control data DA from the calculation controlling circuit 20d is fed to a D/A converter 31 to be converted into a corresponding analog voltage VDA, which is commonly fed to anodes of the correction LEDs 24a, 24b. A cathode of the correction LED 24a is grounded via a current limiting resistor Ra and a transistor Qa. Likewise, a cathode of the correction LED 24b is grounded via a current limiting resistor Rb and a transistor Qb. The calculation controlling circuit 20d controllably turns the transistors Qa, Qb on and off.

The spectral luminometer 61 constructed as above is connected with a personal computer 27d and controlled via the calculation controlling circuit 20d by a loaded correction program at the time of correcting the S-shaped characteristic. Similar to the above, the correction program causes a plurality of different LED control data DA to be fed to the driving circuit 25d and causes the correction LEDs 24a, 24b to individually and simultaneously emit lights at a plurality of different illuminances with the shutter 19 closed. Illuminances on the pixel surfaces of the pixels S1 to Sn illuminated by the emitted lights of a plurality of intensities cover an illuminance range received by a measurement range of the luminometer.

In this embodiment, upon a correction, it is assumed that the resistance values of the current limiting resistors Ra, Rb are set equal to each other, the correction LEDs 24a, 24b are devices having characteristics aligned with each other and, accordingly, drive currents Ia, Ib flowing through the correction LEDs 24a, 24b become equal to each other, and the correction LEDs 24a, 24b emit lights substantially at the same luminance. It is further assumed that the respective correction LEDs 24a, 24b are turned on at nine intensities k=0 to 8 shown in TABLE-2. It is assumed that A(k, a), A(k, b) denote outputs of an arbitrary pixel i (the pixel numbers i are left out below in order to facilitate the following description) when the respective correction LEDs 24a, 24b are individually turned on at the respective intensities k and A(k, a+b) denotes outputs when they are simultaneously turned on at the respective intensities k. It is further assumed that outputs A(O) when the correction LEDs 24a, 24b are off are offsets, and B(k, a)=A(k, a)−A(0), B(k, b)=A(k, b)−A(0), B(k, a+b)=A(k, a+b)−A(0) denote offset-corrected outputs obtained by subtracting the offsets. In the following description, B(k, s) denotes the offset-corrected outputs, and "s" representing the states of the correction LEDs 24a, 24b denotes any of "a", "b", "a+b" and "av", which is an output when the correction LED 24a is singly turned on, when the correction LED 24b is singly turned on, when the correction LEDs 24a, 24b are simultaneously turned on, and an average output when the correction LEDs 24a, 24b are individually turned on.

Figure 13:
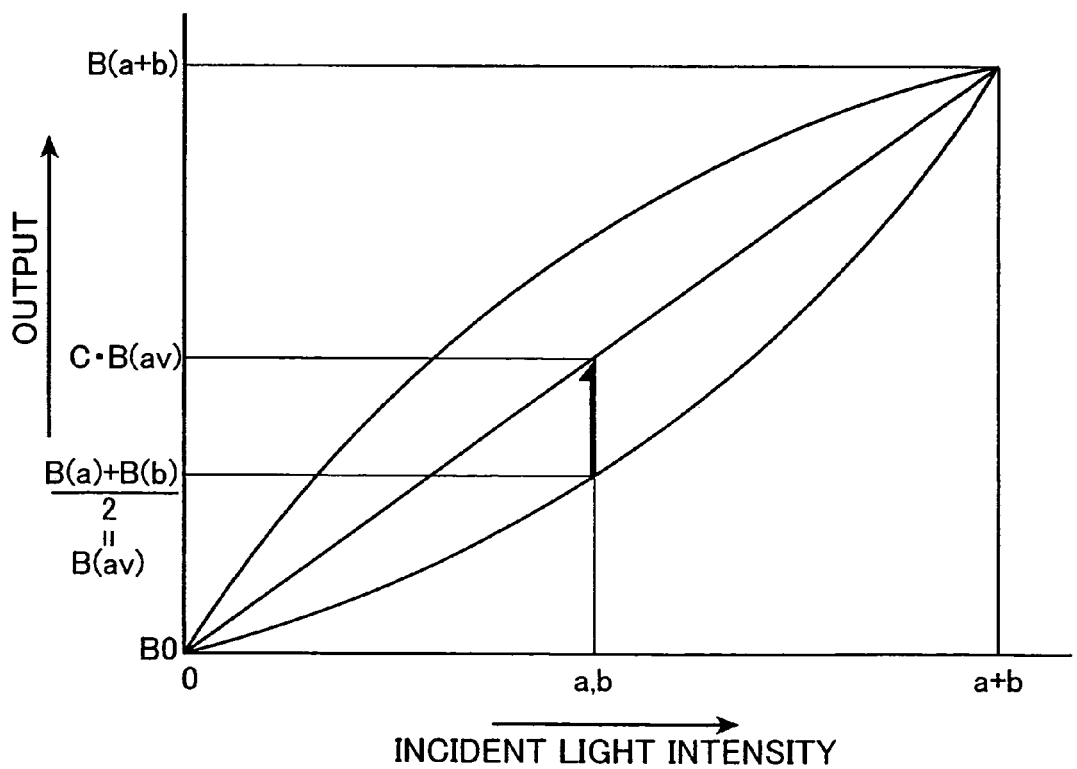
FIG. 13 is a graph showing a concept of correction to be made in the spectral luminometer shown in FIG. 11.

Accordingly, B(k, a+b)=B(k, a)+B(k, b) if a system has linearity, but this relationship does not hold because this system has non-linearity. Accordingly, a linearity correction among three points B=0, B(k, av), B(k, a) is made by calculating such a correction coefficient Ci that B(k, a+b)= [B(k, a)+B(k, b)]*Ci. A concept of this correction is shown in FIG. 13.

Figure 14:
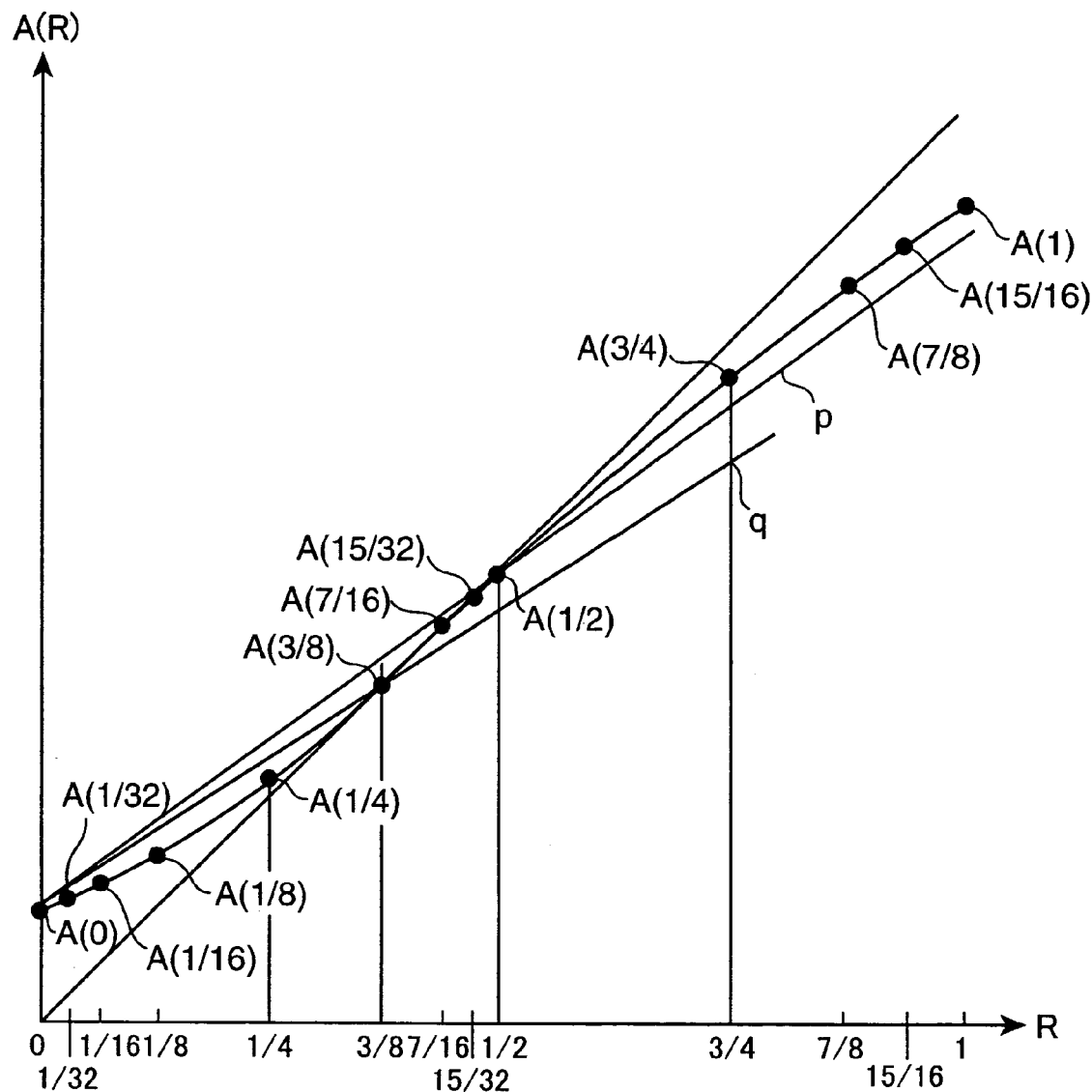
FIG. 14 is a graph showing an exemplary input/output relationship obtained upon correcting an input/output characteristic of a CCD.

FIG. 14 shows an incident/output relationship of an output A (R) in relation to an incident light level incident on an arbitrary pixel i and shown in a full scale ratio R. For example, if [0, A(0)], [1/4, A(1/4)] and [1/2, A(1/2)] are located on a straight line p, there is linearity among these three points. Unless otherwise, a linearity correction among three points is made by calculating such a correction coefficient Ci that A(1/2)=2*A(1/4)*Ci(R). Likewise, if [0, A(0)], [3/8, A(3/8)] and [3/4, A(3/4)] are located on a straight line q, there is linearity among these three points. Unless otherwise, a linearity correction among three points is made by calculating such a correction coefficient Ci that A(3/4)=2*A(3/8)*Ci(R).

Upon a correction, the driving circuit 25d is adjusted such that the offset-corrected output B(k, a+b) at the maximum intensity (k=8) becomes a full scale of the measurement range. Thereafter, the LED control data DA are fed such that ratios R of outputs when the correction LEDs 24a, 24b are individually driven and when the correction LEDs 24a, 24b are simultaneously driven to the full scale (F.S.) take values approximately shown in TABLE-2.

TABLE 2

| k | Individual Emission Ratio to F.S. | Average Output | Simultaneous Emission F.S./R | Output Sum |
|---|---|---|---|---|
| 0 | 0 | B(0) = 0 | 0 | B(0) = 0 |
| 1 | 1/32 | B(1, av) = [B(1, a) + B(1, b)]/2 | 1/16 | B(1, a + b) |
| 2 | 1/16 | B(2, av) = [B(2, a) + B(2, b)]/2 | 1/8 | B(2, a + b) |
| 3 | 1/8 | B(3, av) = [B(3, a) + B(3, b)]/2 | 1/4 | B(3, a + b) |
| 4 | 1/4 | B(4, av) = [B(4, a) + B(4, b)]/2 | 1/2 | B(4, a + b) |
| 5 | 3/8 | B(5, av) = [B(5, a) + B(5, b)]/2 | 3/4 | B(5, a + b) |
| 6 | 7/16 | B(6, av) = [B(6, a) + B(6, b)]/2 | 7/8 | B(6, a + b) |
| 7 | 15/32 | B(7, av) = [B(7, a) + B(7, b)]/2 | 15/16 | B(7, a + b) |

TABLE 2-continued

| k | Individual Emission Ratio to F.S. | Average Output | Simultaneous Emission F.S./R | Output Sum |
|---|---|---|---|---|
| 8 | 1/2 | B(8, av) = [B(8, a) + B(8, b)]/8 | 1 | B(8, a + b) ≈ F.S. |

In this way, the offset-corrected outputs B(k, a). B(k, b), B(k, a+b), B(k, av) are calculated at nine emission intensities k=0 to 8. Based on these offset-corrected outputs, local correction coefficients C'(L)=B(k, a+b)/[B(k, a)+B(k, b)] corresponding to the output levels L=0 to 9 shown in TABLE-3 are calculated. C'(L)=1 for all the output levels if a system has linearity.

TABLE 3

| L | Ratio to F.S | Output Level Y(L) | Local Correction Coefficient C'(L) | Correction Coefficient E[Y](L) |
|---|---|---|---|---|
| 0 | 0 | Y(0) = B(0) = 0 | | E[Y(0)] = 1 |
| 1 | 1/32 | Y(1) = B(1, av) | C'(1) = B(1, a + b)/[B(1, a) + B(1, b)] | E[Y(1)] = C'(1) * E[B(1, a + b)] |
| 2 | 1/16 | Y(2) = B(2, av) | C'(2) = B(2, a + b)/[B(2, a) + B(2, b)] | E[Y(2)] = C'(2) * E[B(2, a + b)] |
| 3 | 1/8 | Y(3) = B(3, av) | C'(3) = B(3, a + b)/[B(3, a) + B(3, b)] | E[Y(3)] = C'(3) * E[B(3, a + b)] |
| 4 | 1/4 | Y(4) = B(4, av) | C'(4) = B(4, a + b)/[B(4, a) + B(4, b)] | E[Y(4)] = C'(4) |
| 5 | 1/2 | Y(5) = B(4, a + b) | | E[Y(5)] = 1 |
| 6 | 3/4 | Y(6) = B(5, a + b) | C'(6) = [B(5, a) + B(5, b)]/B(5, a + b) | E[Y(6)] = C'(6) * E[B(5, av)] |
| 7 | 7/8 | Y(7) = B(6, a + b) | C'(7) = [B(6, a) + B(6, b)]/B(6, a + b) | E[Y(7)] = C'(7) * E[B(6, av)] |
| 8 | 15/16 | Y(8) = B(7, a + b) | C'(8) = [B(7, a) + B(7, b)]/B(7, a + b) | E[Y(8)] = C'(8) * E[B(7, av)] |
| 9 | 1 | Y(9) = B(8, a + b) | C'(9) = [B(8, a) + B(8, b)]/B(8, a + b) | E[Y(9)] = C'(9) * E[B(8, av)] |

Subsequently, correction coefficients E[Y(L)] corresponding to the respective output levels Y(L) are calculated based on data obtained by a correction data measuring procedure to be described later. The correction is made to accumulate the preceding results step by step such that the output levels Y(L) conform to a straight line connecting the output level Y(0) when the correction LEDs are off and the output Y(5)=B(4, a+b) at the 1/2 emission. First, E[Y(4)], E[Y(3)], E[Y(2)] and E[Y(1)] are calculated and then E[Y(6)], E[Y(7)], E[Y(8)] and E[Y(9)] located on an extension of the above straight line are calculated and saved in the calculation controlling circuit 20d.

The above points are specifically described below. The correction data measuring procedure is as follows.

1. Measure a maximum luminance of the measurement range and save a maximum value B(Max) of the offset-corrected outputs.
2. Close the shutter 19.
3. Set the drive currents Ia, Ib of the correction LEDs 24a, 24b such that the outputs of the respective pixels when the correction LEDs 24a, 24b are simultaneously turned on approximate to B(Max), and save the output Y(9)=B(8, a+b) at this time and the outputs B(8, a), B(8, b) when the correction LEDs 24a, 24b are individually turned on.
4. Set the drive currents Ia, Ib of the correction LEDs 24a, 24b such that the outputs of the respective pixels when the correction LEDs 24a, 24b are simultaneously turned on take values of about Y(9)/2 and save the output Y(5)=B(4, a+b) at this time and the outputs B(4, a), B(4, b) when the correction LEDs 24a, 24b are individually turned on.
5. Set the drive currents Ia, Ib of the correction LEDs 24a, 24b such that the outputs of the respective pixels when the correction LEDs 24a, 24b are simultaneously turned on take values of about Y(9)/4 and save the output B(3, a+b) at this time and the outputs B(3, a), B(3, b) when the correction LEDs 24a, 24b are individually turned on.
6. Set the drive currents Ia, Ib of the correction LEDs 24a, 24b such that the outputs of the respective pixels when the correction LEDs 24a, 24b are simultaneously turned on take values of about Y(9)/8 and save the output B(2, a+b) at this time and the outputs B(2, a), B(2, b) when the correction LEDs 24a, 24b are individually turned on.
7. Set the drive currents Ia, Ib of the correction LEDs 24a, 24b such that the outputs of the respective pixels when the correction LEDs 24a, 24b are simultaneously turned on take values of about Y(9)/16 and save the output B(1, a+b) at this time and the outputs B(1, a), B(1, b) when the correction LEDs 24a, 24b are individually turned on.
8. Set the drive currents Ia, Ib of the correction LEDs 24a, 24b such that the outputs of the respective pixels when the correction LEDs 24a, 24b are simultaneously turned on take values of about Y(9)*3/4 and save the output B(5, a+b) at this time and the outputs B(5, a), B(5, b) when the correction LEDs 24a, 24b are individually turned on.
9. Set the drive currents Ia, Ib of the correction LEDs 24a, 24b such that the outputs of the respective pixels when the correction LEDs 24a, 24b are simultaneously turned on take values of about Y(9)*7/8 and save the output B(6, a+b) at this time and the outputs B(6, a), B(6, b) when the correction LEDs 24a, 24b are individually turned on.
10. Set the drive currents Ia, Ib of the correction LEDs 24a, 24b such that the outputs of the respective pixels when the correction LEDs 24a, 24b are simultaneously turned on take values of about Y(9)*15/16 and save the output B(7, a+b) at this time and the outputs B(7, a), B(7, b) when the correction LEDs 24a, 24b are individually turned on.

A procedure of calculating the correction coefficients E[Y(L)] from the thus calculated measurement data is as follows.

1. Calculate the correction coefficient E(4)=C'(4) at L=4 (1/4 emission) and Y(4)=[B(4, a)+B(4, b)]/2.
2. Calculate the correction coefficient E(3)=C'(3)*E[B(3, a+b)] at L=3 and Y(3)=B(3, av). E[B(3, a+b)] is the correction coefficient for Y=B(3, a+b) obtained by applying a linear interpolation to the correction coefficients at L=4 and 5.
3. Calculate the correction coefficient E(2)=C'(2)*E[B(2, a+b)] at L=2 and Y(2)=B(2, av).
   E[B(2, a+b)] is the correction coefficient for Y=B(2, a+b) obtained by applying a linear interpolation to the correction coefficients at L=3 and 4.
4. Calculate the correction coefficient E(1)=C'(1)*E[B(1, a+b)] at L=1 and Y(1)=B(1, av).
   E[B(1, a+b)] is the correction coefficient for Y=B(1, a+b) obtained by applying a linear interpolation to the correction coefficients at L=2 and 3.
5. Calculate the correction coefficient E(6)=C'(6)*E[B(5, av)] at L=6 and Y(6)=B(5, a+b).
   E[B(5, av)] is the correction coefficient for Y=B(5, av) obtained by applying a linear interpolation to the correction coefficients at L=4 and 5.
6. Calculate the correction coefficient E(7)=C'(7)*E[B(6, av)] at L=7 and Y(7)=B(6, a+b).
   E[B(6, av)] is the correction coefficient for Y=B(6, av) obtained by applying a linear interpolation to the correction coefficients at L=4 and 5.
7. Calculate the correction coefficient E(8)=C'(8)*E[B(7, av)] at L=8 and Y(8)=B(7, a+b).
   E[B(7, av)] is the correction coefficient for Y=B(7, av) obtained by applying a linear interpolation to the correction coefficients at L=4 and 5.
8. Calculate the correction coefficient E(9)=C'(9)*E[B(8, av)] at L=9 and Y(9)=B(8, a+b).
   E[B(8, av)] is the correction coefficient for Y=B(8, av) obtained by applying a linear interpolation to the correction coefficients at L=4 and 5.
9. Generate a correspondence table of the output levels Y(L) and the correction coefficients E[Y] based on the results of the steps 1 to 8 above.

As described above, the integration times of the photoelectrons of the CCD are frequently selected according to the intensity of the measurement light in the spectral luminometer. In the case that the non-linearity of the CCD depends on the integration time T, the correspondence table of the output levels Y(L) and the correction coefficients E[Y] is generated for each of the selectable integration times T and saved in the calculation controlling circuit 20d.

At the time of a measurement, the calculation controlling circuit 20d measures the offset level and the measurement light for the integration time T set by the user and saves offset-corrected signal levels Bi of the respective pixels i. The calculation controlling circuit 20d further calculates the correction coefficients Ei(Bi) corresponding to the saved signal levels Bi by interpolating the correction coefficients Ei(0) to Ei(9) corresponding to the saved levels Y(0) to Y(9), and calculates data B' having non-linearity errors corrected by Bi'=Bi*Ei.

Specifically, the measurement is conducted as follows.
1. Read the integration time T set by the user.
2. Measure the offset for the set integration time T with the shutter 19 closed and calculate the output Ao.
3. Measure the measurement light for the set integration time T with the shutter 19 opened and calculate the output A.
4. Calculate the offset-corrected output B=A−Ao.
5. Calculate the correction coefficient E(B) corresponding to the output B of the measurement light by applying an interpolation to the correspondence table of the output levels Y(L) and the correction coefficients E[Y] for the set integration time T.
6. Calculate a corrected intensity signal B' by B'=E(B)*B.

As described above, the correspondence table of the output levels Y(L) and the correction coefficients E[Y] are generated by first obtaining data at the full emission and those in a turned-off state having a relatively high precision and then obtaining intermediate data by successively applying an interpolation using the already obtained known data. Although errors are accumulated in the data of intermediate values, it is not a problem at the measurement precision level of the spectral luminometer. In this way, the S-shaped characteristic caused by the saturation and a dark current offset of the light receiving sensor array 32 of CCD can be corrected.

The number of the correction LEDs is not limited to two, and even more correction LEDs may be used, wherein the characteristics (emission luminance levels) of these correction LEDs may not be aligned with each other. For instance, these characteristics may be set at a specified ratio of, e.g. 1:2:4: . . . . It is sufficient to set these characteristics such that necessary data points can be efficiently obtained with a small number of devices.

The non-linearity correction of the fifth embodiment of the present invention is applicable not only to the spectral luminometer 61, but also to the spectral luminometer 71 as shown in FIG. 9. Further, this non-linearity correction is applicable not only for the non-linearity errors of the linear CCD incorporated into the polychrometers 16, 36, but also for that of the two-dimensional CCD incorporated into the image measuring apparatus 51 as shown in FIG. 10. The correction coefficients calculated and saved at the time of production are used for the non-linearity correction at the time of a measurement. However, the user makes a correction prior to the measurement and, in this case, the correction is made at a working temperature. Thus, the non-linearity correction is not influenced by temperature even if having a temperature dependency.

Further, a relationship of the signal levels B and the correction coefficients E(B) may be expressed by a function F(B). The following function may be thought as such a function.

$$F(B) = F1(B) = P0 + P1*B + P2*B^2 \quad \text{if } B < B1$$
$$= F2(B) = Q0 + Q1*B + Q2*B^2 \quad \text{if } B > B2$$
$$= F3(B) = a*B + b \quad \text{if } B1 < B < B2$$

where a=[F1(B1)−F2(B2)]/[B1−B2], and
b=[B1*−F2(B2)−B2*F1(B1)]/[B1-B2].

Figure 15:
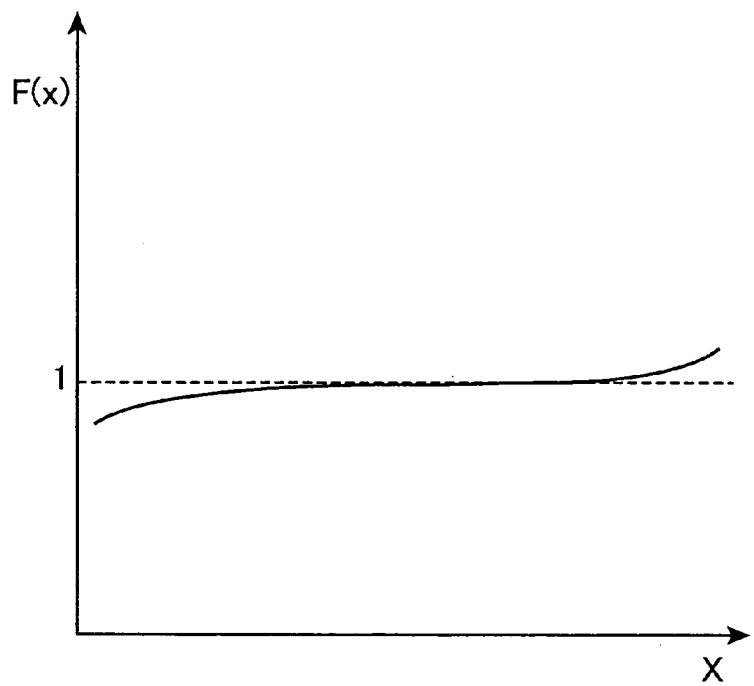
FIG. 15 is a graph showing an exemplary quadratic function for correcting the input/output characteristic of the CCD.
Figure 16:
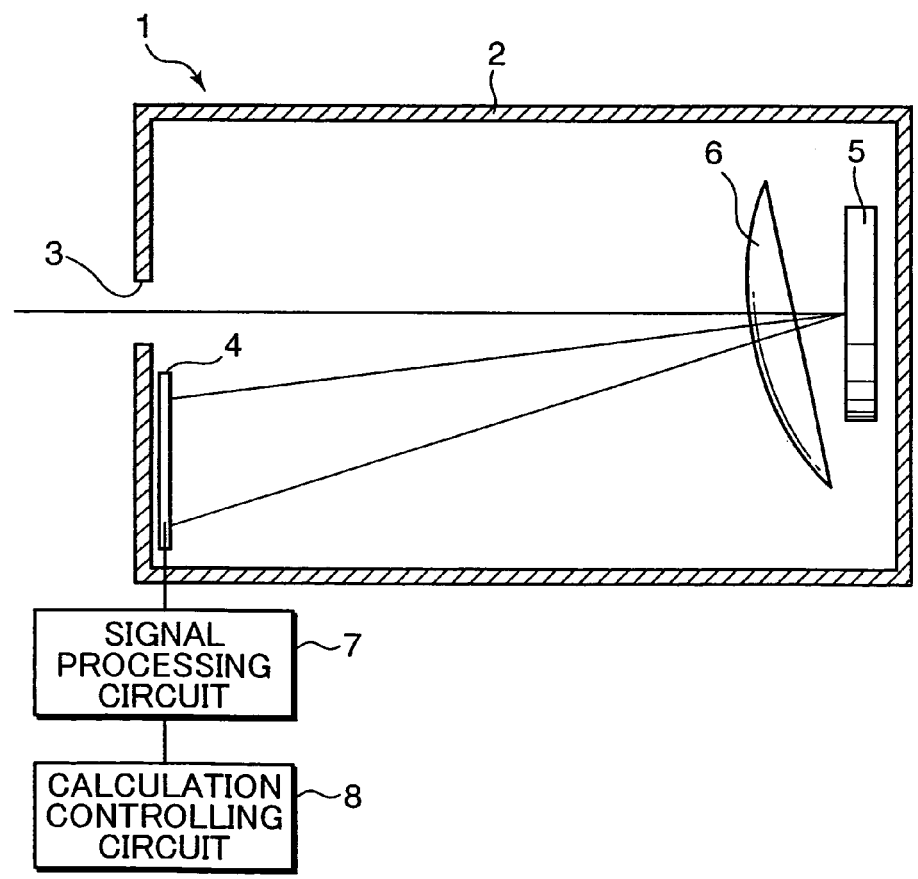
FIG. 16 is a sectional view showing a schematic construction of a polychrometer generally in use.

Since the linearity is generally good in the middle of the range and poor at the upper and lower ends thereof as shown in FIG. 18, this function is the one obtained by approximating the outputs at the upper and lower ends by a quadratic equation and by a straight line at the middle range. Since coefficients P0 to P2, Q0 to Q2 and two threshold values B1, B2 for determining the function are so determined as to minimize a square sum $\Sigma(d(k)^2)$ for all the values of k if it is assumed that remaining linearity errors after the correction is: d(k)=F[B(k, a+b)]*B(k, a+b)/{F[B(k, a)]*B(k, a)+F[B(k, b)]*B(k, b)}−1. An example of this function F(B) is shown in FIG. 15.

As described above, a light measuring apparatus for measuring an illuminance level of light being measured, comprises one or more correction light emitters for illuminating an optical sensor, and a calculation controller for, at the time of a correction, calculating correction values at the respective illuminance levels based on sensor output levels expected at the respective illuminance levels and actual sensor output levels while successively turning the correction light emitter on at a plurality of illuminance levels whose illuminance ratios are at least known and, at the time of an actual measurement, correcting the sensor output level by the corresponding correction value to obtain a measurement output.

By taking the above construction, upon correcting non-linearity in a light measuring apparatus realized as a spectral luminometer and a spectral colorimeter, one or more correction light emitters are used and successively turned on at the plurality of illuminance levels, whose illumination ratios are at least known. The non-linearity includes the discontinuity of an input/output characteristic resulting from the switching of gains, for example, in the case that an amplifier for amplifying a photocurrent performs amplification while selecting a suitable gain from a plurality of gains depending on an incident light intensity level. The non-linearity is also caused by characteristics of an optical sensor and an amplifier such as the saturation of a photoelectrically converting characteristic of the optical sensor.

The illumination ratios are not absolute illumination levels such as a certain watt. For example, in the case that ten correction light emitters have illuminance levels equal to each other and half of them, i.e. five are turned on, the illumination level is half of the one obtained when all ten correction light emitters are turned on. In another exemplary case where three correction light emitters having a ratio of the illuminance levels of 1:2:4, eight illuminance levels of 0, 1, 2, 3, 4, 5, 6, 7 are available because of eight patterns of turning the correction light emitter on and off. Even if a single correction light emitter is used, the level of a drive current can be switched at a plurality of stages. It is sufficient that a relative ratio of the switchable illuminance levels are known. Further, the state where all the correction light emitters are turned on or the correction light emitter is turned on at full power may be set as a maximum value of the sensor input level, i.e. a dynamic range.

Upon the correction, the calculation controller first causes the correction light emitter to successively be turned on by an arbitrary combination or by an arbitrary current value, whereby the sensor output values at the plurality of illuminance levels are obtained. Subsequently, the calculation controller calculates the correction values at the respective levels (turned-on state) based on the sensor output levels expected at the respective illuminance levels and the actual sensor output levels. Specifically, the sensor output levels are expressed, for example, in the form of 8-bit digital data. In the case of using ten correction light emitters whose illumination levels are equal to each other, the illuminance level is expressed by 255 in decimal data if all ten correction light emitters are turned on, by 128 when half of them, i.e. five are turned on, by 0 when none of them is turned on. In this way, expected values at the respective illuminance values are already set, and deviations from these expected values or ratios to them are calculated as the correction values.

At the time of an actual measurement, the sensor output level is corrected by applying addition, subtraction, multiplication or division using the corresponding correction value to obtain the measurement output. At this time, an interpolation calculation or the like may be suitably performed in the absence of the correction value agreeing with the actual sensor output level.

Accordingly, the non-linearity can be highly precisely and efficiently corrected without requiring any special facility.

Another light measuring apparatus may be further provided with a variable gain amplifier for amplifying the output of the optical sensor in accordance with a plurality of different gains. The calculation controller causes the correction light emitter to emit light at the plurality of illuminance levels having the known illuminance ratios, measures the sensor output levels at the respective illuminance levels in accordance with the plurality of gains of the variable gain amplifier, and calculates the correction value for the sensor output level of the light being measured from a ratio of measurement results at the respective illuminance levels in accordance with the respective gains.

In the light measuring apparatus having the above construction in which an output from the optical sensor is amplified in accordance with a plurality of gains using the variable gain amplifier in order to enlarge the dynamic range within which the light can be measured, an input/output characteristic of the variable gain amplifier becomes discontinuous between the adjacent gains to cause non-linearity as a result of the switching of the gains realized by the switching of feedback resistors or the switching of an input resistor.

Accordingly, the correction light emitter is caused to emit light at the plurality of illuminance levels having the known illumination ratios to produce illumination light for correction. Then, the sensor output levels are measured at the respective illuminance levels in accordance with the plurality of gains. Deviations of the measurement results among the plurality of gains whose measurement ranges overlap even at the same illuminance level become clear. The gain ratio of the overlapped measurement ranges is corrected in such a way that a lowest measurement value of the measurement range having a larger gain becomes the same as the highest measurement value of the measurement range having a smaller gain.

Accordingly, the input/output characteristic comes to take the form of one straight line using a plurality of gains, thereby solving a problem of the discontinuity.

In still another light measuring apparatus, the optical sensor includes a sensor array in which a plurality of pixel sensors are linearly or two-dimensionally arrayed; a monitoring optical sensor having linearity is provided adjacent to the optical sensor, and illuminatable by the illumination light from the correction light emitter; and the calculation controller causes the correction light emitter to emit light at the plurality of illuminance levels having the known illuminance ratios, measures the sensor output levels at the respective illuminance levels, and sets ratios of the sensor outputs of the respective pixel sensors to the sensor output of the monitoring optical sensor as the correction values for the sensor output of the light being measured.

In the thus constructed light measuring apparatus having the optical sensor including the sensor array in which a plurality of pixel sensors are linearly or two-dimensionally arrayed, and usable as a spectral luminometer or a spectral colorimeter, the monitoring optical sensor adjacent to the optical sensor and illuminatable by the illumination lights from the correction light emitter is separately provided in order to correct the output from the optical sensor having linearity and the CCD in which a common amplifier can be used among a plurality of pixels to make this output linear.

This monitoring optical sensor has good linearity by, for example, including amplifiers characteristic of silicon photodiodes.

Accordingly, the non-linearity of many pixel sensors of the optical sensor can be easily corrected by setting the ratios of the sensor outputs of the respective pixel sensors to the sensor outputs of the monitoring optical sensor at the respective illuminance levels as the correction values for the sensor output in response to the light being measured.

In a further another light measuring apparatus, a plurality of correction light emitters are provided; and the calculation controller calculates the sensor output levels when the optical sensor is individually illuminated by the respective correction light emitter and the one when the optical sensor is simultaneously illuminated by the respective correction light emitter, calculates a signal ratio of a sum of the sensor output levels when the optical sensor is individually illuminated by the respective correction light emitter to the output level when the optical sensor is simultaneously illuminated by the respective correction light emitter, performs the above processing at the plurality of illuminance levels having the known illuminance ratios, and calculates the correction values for the sensor output level of the light being measured based on the calculated sensor output levels and signal ratio data.

With this construction, the non-linearity near a saturated output level of the optical sensor or a dark current offset level can be corrected.

In a still further light measuring apparatus, a shield for shutting off the light being measured while the correction light emitter is on is provided. With this construction, the non-linearity can be precisely corrected based only on the illumination light for correction from the correction light emitter without being influenced by an incident light from the outside.

In a still another light measuring apparatus, the illumination light by the correction light emitter is directly reaching light from the correction light emitter. With this construction, the illumination light from the correction light emitter directly reaches the optical sensor. Accordingly, if a wavelength divider or a short-wavelength cut filter is provided in the spectral luminometer or the spectral calorimeter, the illumination light directly reaches the optical sensor without by way of the short-wavelength cut filter. Thus, the optical sensor is uniformly illuminated without the illumination light level being reduced only at specific pixel sensors. Therefore, it is not necessary to turn the correction light source on at different intensities for each sensor. Further, a single-color light source such as an LED can be used.

Also, a non-linearity correcting method for correcting the non-linearity of a light measuring apparatus, comprising the steps of: successively turning one or more correction light emitters at a plurality of illuminance levels whose illuminance ratios are at least known at the time of a correction to illuminate an optical sensor at the plurality of illuminance levels, calculating correction values at the respective illuminance levels based on sensor output levels expected at the respective illuminance levels and actual sensor output levels, and correcting the sensor output level by the corresponding correction value to obtain a measurement output at the time of an actual measurement.

In this method, upon correcting non-linearity in a light measuring apparatus realized as a spectral luminometer and a spectral colorimeter, one or more correction light emitters are used. The non-linearity includes the discontinuity of an input/output characteristic resulting from the switching of gains, for example, in the case that an amplifier for amplifying a photocurrent performs amplification while selecting a suitable gain from a plurality of gains depending on an incident light intensity level. The non-linearity is also caused by characteristics of an optical sensor and an amplifier such as the saturation of a photoelectrically converting characteristic of the optical sensor.

Upon the correction, these correction light emitters are first successively turned on at the plurality of illuminance levels whose illuminance ratios are at least known, whereby the sensor outputs at the plurality of illuminance levels can be obtained. Subsequently, the correction values at the respective illuminance levels (turned-on states) are calculated based on the sensor output levels expected at the respective illuminance levels and actual sensor output levels.

At the time of an actual measurement, the sensor output level is corrected by applying addition, subtraction, multiplication or division using the corresponding correction value to obtain the measurement output. At this time, an interpolation calculation or the like may be suitably performed in the absence of the correction value agreeing with the actual sensor output level.

Accordingly, the non-linearity can be highly precisely and efficiently corrected without requiring any special facility.

In another non-linearity correcting method, the plurality of correction light emitters are gradation-controlled at the illuminance levels having the known illuminance ratios. With this method, main data points can be obtained even if a small number of the correction light emitters are used. Thus, the correction can be highly precisely and efficiently made.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds are therefore intended to embraced by the claims.

What is claimed is:

1. A light measuring apparatus for measuring an illuminance level of light, the apparatus comprising:
one or more correction light emitters which illuminate an optical sensor at predetermined illuminance levels, the illuminance levels having known illuminance ratios;
a calculation controller configured to calculate correction values at the respective illuminance levels based on expected and actual sensor output levels at the respective illuminance levels;
the calculation controller configured to successively turn-on the correction light emitter at the respective illuminance levels, and correct the sensor output level by the corresponding correction value to obtain a measurement output; and
a variable gain amplifier configured to amplify the output of the optical sensor in accordance with a plurality of different gains,
wherein the calculation controller measures the sensor output levels at the respective illuminance levels in accordance with the plurality of different gains, and calculates the correction value for the sensor output level based on a ratio of measurement results at the respective illuminance levels in accordance with the respective gains.

2. A light measuring apparatus for measuring an illuminance level of light, the apparatus comprising:
   one or more correction light emitters which illuminate an optical sensor at predetermined illuminance levels, the illuminance levels having known illuminance ratios;
   a calculation controller configured to calculate correction values at the respective illuminance levels based on expected and actual sensor output levels at the respective illuminance levels;
   the calculation controller configured to successively turn-on the correction light emitter at the respective illuminance levels, and correct the sensor output level by the corresponding correction value to obtain a measurement output; and
   a monitoring optical sensor having linearity, disposed adjacent to the optical sensor, said monitoring optical sensor configured to receive the illumination light from the correction light emitter.

3. A light measuring apparatus for measuring an illuminance level of light, the apparatus comprising:
   a plurality of correction light emitters which illuminate an optical sensor at predetermined illuminance levels, the illuminance levels having known illuminance ratios;
   a calculation controller configured to calculate correction values at the respective illuminance levels based on expected and actual sensor output levels at the respective illuminance levels;
   the calculation controller configured to successively turn-on the correction light emitter at the respective illuminance levels, and correct the sensor output level by the corresponding correction value to obtain a measurement output; and
   wherein the calculation controller
      (a) calculates the sensor output levels when the optical sensor is individually illuminated by the respective correction light emitter and when the optical sensor is simultaneously illuminated by the respective correction light emitter;
      (b) calculates a signal ratio of a sum of the sensor output levels when the optical sensor is individually illuminated by the respective correction light emitter to the output level when the optical sensor is simultaneously illuminated by the respective correction light emitter;
      (c) performs steps (a)-(b) at the plurality of illuminance levels having the known illuminance ratios, and
      (d) calculates the correction values for the sensor output level of the light being measured based on the calculated sensor output levels and signal ratio data.

4. A light measuring apparatus for measuring an illuminance level of light, the apparatus comprising:
   one or more correction light emitters which illuminate an optical sensor at predetermined illuminance levels, the illuminance levels having known illuminance ratios;
   a calculation controller configured to calculate correction values at the respective illuminance levels based on expected and actual sensor output levels at the respective illuminance levels;
   the calculation controller configured to successively turn-on the correction light emitter at the respective illuminance levels, and correct the sensor output level by the corresponding correction value to obtain a measurement output; and
   a shield which shuts off the light being measured while the correction light emitter is on.

5. A light measuring apparatus for measuring an illuminance level of light, the apparatus comprising:
   one or more correction light emitters which illuminate an optical sensor at predetermined illuminance levels, the illuminance levels having known illuminance ratios;
   a calculation controller configured to calculate correction values at the respective illuminance levels based on expected and actual sensor output levels at the respective illuminance levels; and
   the calculation controller configured to successively turn-on the correction light emitter at the respective illuminance levels, and correct the sensor output level by the corresponding correction value to obtain a measurement output,
   wherein the illumination light from the correction light emitter directly reaches the optical sensor.

6. A method for correcting the non-linearity of a light measuring apparatus, comprising the steps of:
   successively turning one or more correction light emitters at a plurality of illuminance levels to illuminate an optical sensor at the illuminance levels corresponding to known illuminance ratios;
   calculating correction values at the respective illuminance levels based on expected and actual sensor output levels at the respective illuminance levels; and
   correcting the sensor output level by the corresponding correction value to obtain a measurement output,
   wherein the calculation controller measures the sensor output levels at the respective illuminance levels in accordance with a plurality of different gains, and calculates the correction value for the sensor output level based on a ratio of measurement results at the respective illuminance levels in accordance with the respective gains.

7. A method according to claim 6, wherein one or more correction light emitters are controlled in a stepwise manner at the illuminance levels.

8. The apparatus according to claim 2, wherein the calculation controller causes the correction light emitter to emit light at the plurality of illuminance levels having the known illuminance ratios, measures the sensor output levels at the respective illuminance levels, and sets ratios of the sensor outputs of the respective pixel sensors to the sensor output of the monitoring optical sensor as the correction values for the sensor output of the light being measured.

* * * * *

UNITED STATES PATENT AND TRADEMARK OFFICE
CERTIFICATE OF CORRECTION

PATENT NO. : 7,286,215 B2
APPLICATION NO. : 10/841189
DATED : October 23, 2007
INVENTOR(S) : Kenji Imura It is certified that error appears in the above-identified patent and that said Letters Patent is hereby corrected as shown below:

<u>In the Claims</u>

Column 24, in claim 6, line 3, after "successively turning" insert --on--.

Signed and Sealed this

Twenty-ninth Day of April, 2008

JON W. DUDAS
*Director of the United States Patent and Trademark Office*

UNITED STATES PATENT AND TRADEMARK OFFICE
CERTIFICATE OF CORRECTION

PATENT NO. : 7,286,215 B2
APPLICATION NO. : 10/841189
DATED : October 23, 2007
INVENTOR(S) : Kenji Imura It is certified that error appears in the above-identified patent and that said Letters Patent is hereby corrected as shown below:

On the Title Page

Column 1, item (76), delete "3-91, Daisennishi-machi, Sakai-shi, Osaka 590-8551 (JP)" and substitute --Toyohashi-shi (JP)-- in its place.

In the Claims

Column 24, in claim 6, line 3, after "successively turning" insert --on--.

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 7,286,215 B2  Page 1 of 1
APPLICATION NO. : 10/841189
DATED : October 23, 2007
INVENTOR(S) : Kenji Imura It is certified that error appears in the above-identified patent and that said Letters Patent is hereby corrected as shown below:

On the Title Page

Column 1, item (76), delete "3-91, Daisennishi-machi, Sakai-shi, Osaka 590-8551 (JP)" and substitute --Toyohashi-shi (JP)-- in its place.

In the Claims

Column 24, in claim 6, line 29, after "successively turning" insert --on--.

This certificate supersedes the Certificates of Correction issued April 29, 2008 and October 7, 2008.

Signed and Sealed this

Twenty-first Day of October, 2008

JON W. DUDAS
*Director of the United States Patent and Trademark Office*